United States Patent [19]
Chesnut et al.

[11] Patent Number: 6,017,754
[45] Date of Patent: Jan. 25, 2000

[54] SYSTEM FOR ISOLATING AND IDENTIFYING EUKARYOTIC CELLS TRANSFECTED WITH GENES AND VECTORS, HOST CELLS AND METHODS THEREOF

[75] Inventors: Jonathan D. Chesnut, Encinitas; James P. Hoeffler, Carlsbad, both of Calif.

[73] Assignee: Invitrogen Corporation, Carlsbad, Calif.

[21] Appl. No.: 08/518,835

[22] Filed: Aug. 24, 1995

[51] Int. Cl.[7] .......................... C12Q 1/68; G01N 33/566; C12N 5/10; C07K 16/00
[52] U.S. Cl. .......................... 435/320.1; 435/6; 435/7.2; 435/7.21; 435/328; 435/975; 530/387.3; 530/388.9; 536/23.1
[58] Field of Search .......................... 435/320.1, 6, 7.2, 435/7.21, 328, 975; 530/387.3, 388.9; 536/23.1

[56] References Cited

U.S. PATENT DOCUMENTS

| | | |
|---|---|---|
| 5,359,046 | 10/1994 | Capon et al. . |
| 5,409,813 | 4/1995 | Schwartz .............................. 435/7.24 |
| 5,637,481 | 6/1997 | Ledbetter et al. . |
| 5,667,988 | 9/1997 | Barbas et al. . |
| 5,686,279 | 11/1997 | Finer et al. . |
| 5,731,425 | 3/1998 | Brizzard et al. . |

OTHER PUBLICATIONS

Clackson, T., et al., "Making Antiboy Fragments Using Phage Display Libraries", *Nature*, 352:624–628 (1991).

Figini, M., et al., "In Vitro Assembly of Repertoires of Antibody Chains on the Surface of Phage by Renaturation", *J. Mol. Biol.*, 239:68–78 (1994).

Hawkins, R.E., et al., "Selection of Phage Antibodies by Binding Affinity Mimicking Affinity Maturation", *J. Mol. Biol.*, 226:889–896 (1992).

Hoogenboom, H.R., et al., "Building Antibodies from their Genes", *Immunol. Rev.*, 130:41–68 (1992).

Jespers, E.A., et al., "Guiding the Selection of Human Antibodies from Phage Display Repertoires to a Single Epitope of an Antigen", *Biotechnology*, 12:899–903 (1994).

Larrick, J.W., et al., "Rapid Cloning of Rearranged Immunoglobulin Genes From Human Hybridoma Cells Using Mixed Primers and the Polymerase Chain Reaction", *Biochem. Biophys. Res. Comm.*, 160:1250–1256 (1989).

Marks, J.D., et al., "By–Passing Immunization Human Antibodies from V–Gene Libraries Displayed on Phage", *J. Mol. Biol.*, 222:581–597 (1991).

McCafferty, J., et al., "Phage Antibodies: Filamentous Phage Displaying Antibody Variable Domains", *Nature*, 348:552–554 (1990).

Morrison, S.L., et al., "Production and Characterization of Genetically Engineered Antibody Molecules", *Clin. Chem.*, 34:1668–1675 (1988).

Orlandi, R., et al., "Cloning Immunoglobulin Variable Domains for Expression by the Polymerase Chain Reaction", *Proc. Natl. Acad. Sci.*, 86:3833–3837 (1989).

Siegall, C.B., et al., "In Vitro and In Vivo Characterization of BR96 sFv–PE40", *J. Immunol.*, 152:2377–2384 (1994).

Winter, G., et al., "Making Antibodies by Phage Display Technology", *Annu. Rev. Immunol*, 12:433–455 (1994).

Hoogenboom, H.R. et al., "Multi–subunit proteins on the surface of filamentous phage: Methodologies for displaying antibody (Fab) heavy and light chains", *Nucleic Acid Res.*, 19(15):4133–4137 (1991).

Williamson, R.A. et al., "Human monoclonal antibodies against a plethora of viral pathogens from single combinatorial libraries", *Proc. Natl. Acad. Sci. USA*, 90:4141–4145 (1993).

*Primary Examiner*—David Saunders
*Assistant Examiner*—F. Pierre VanderVegt
*Attorney, Agent, or Firm*—Scully, Scott, Murphy & Presser

[57] ABSTRACT

The present invention relates a novel expression system which allows the study of experimental genes of interest on cellular events soon after transfection. The expression system includes a vector which encodes for a recombinant antibody binding unit (rAb). The expression system enables identification and selection of transfected cells from culture to be carried out immediately, within hours, after the transfection

24 Claims, 41 Drawing Sheets

| Feature | Benefit |
|---|---|
| PhOx sFv | This single chain antibody recognizes the hapten, phOx and allows isolation or detection of cells displaying this sFv (Griffiths, et al., 1984; Hoogenboom, et al., 1991) |
| Cytomegalovirus (CMV) immediate early promoter | Permits high-level expression of the sFv in a wide variety of eukaryotic cells |
| Signal peptide (Met-Glu-Thr-Asp-Thr-Leu-Leu-Leu-Trp-Val-Leu-Leu-Leu-Trp-Val-Pro-Gly-Ser-Thr-Gly-Asp) | Signal peptide from murine Ig κ-chain V-J2-C region directs the sFv to the plasma membrane for extracellular display |
| Hemagglutinin A epitope tag (Tyr-Pro-Tyr-Asp-Val-Pro-Asp-Tyr-Ala) | Allows detection of the sFv by monoclonal antibody 12CA5 (Kolodziej and Young, 1991; Niman, et al., 1983) |
| Myc.1 epitope tag (Glu-Gln-Lys-Leu-Ile-Ser-Glu-Glu-Asp-Leu-Asn) | Allows detection of the sFv by the monoclonal antibody 9E10.2 (Evan, et al., 1985) |
| Platelet-derived growth factor receptor transmembrane domain (PDGFR-TM) | Fusion of PDGFR-TM to sFv anchors the antibody to the plasma membrane for display |
| Bovine growth hormone polyadenylation signal | Permits proper processing and polyadenylation of the mRNA for stabilization of the message |
| Ampicillin resistance gene | Allows selection of the plasmid in E. coli |
| ColE1 origin | High copy replication and growth in E. coli |
| Kanamycin resistance gene | Allows selection of the plasmid in E. coli using kanamycin<br><br>Note: this gene will also confer resistance to G418 in mammalian cells |
| SV40 promoter and origin | Permits expression of the kanamycin resistance gene for G418 resistance in mammalian cells<br><br>Allows episomal replication in cells containing SV40 large T antigen |

FIG. 1A-1

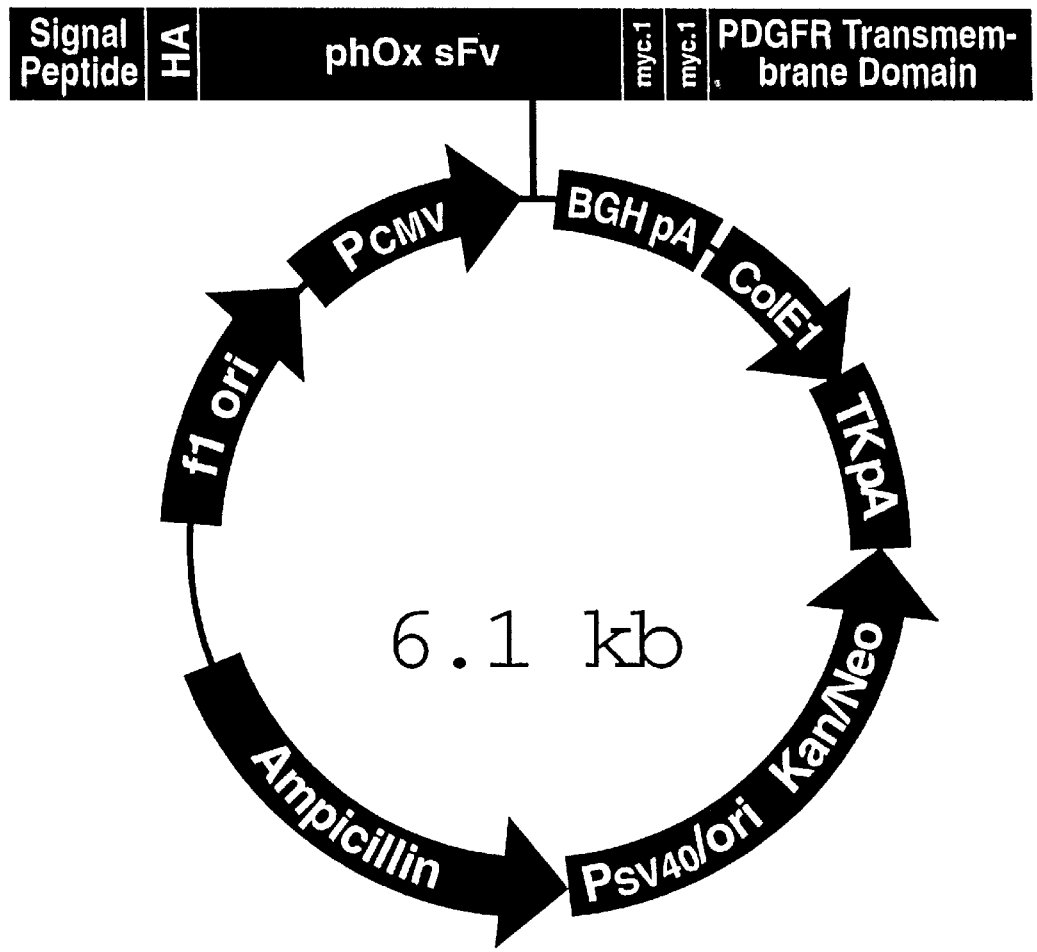

Comments for pHook™-1:
 6115 nucleotides

CMV promoter: bases 1-596
Murine Ig kappa-chain V-J2-C signal peptide: bases 737-799
Hemagglutinin A epitope: bases 800-826
phOx sFv: bases 842-1555
Myc.1 epitope 1: bases 1568-1600
Myc.1 epitope 2: bases 1613-1645
PDGFR transmembrane domain: bases 1646-1795
Bovine growth hormone polyadenylation signal: bases 1853-2081
Col E1 origin: bases 2212-2795
SV40 origin and promoter: bases 4587-4249
Neomycin/Kanamycin resistance gene: bases 4214-3426
Thymidine kinase polyadenylation site: bases 3251-2980
Ampicillin resistance gene: bases 55526-4666
f1 origin: bases 5657-6113

CMV promoter: bases 1-596
T7 promoter: bases 638-657

Murine Ig kappa-chain V-J2-C signal peptide: bases 737-799
Hemagglutinin A epitope: bases 800-826
phOx sFv: bases 842-1555
Myc.1 epitope 1: bases 1568-1600
Myc.1 epitope 2: bases 1613-1645
PDGFR transmembrane domain: bases 1646-1795

SP6 promoter: bases 1831-1848
Bovine growth hormone polyadenylation signal: bases 1853-2081

Col El origin: bases 2212-2795

SV40 origin and promoter: bases 4587-4249
Neomycin/Kanamycin resistance gene: bases 4214-3426
Thymidine kinase polyadenylation site: bases 3251-2980

Ampicillin resistance gene: bases 5526-4666
fl origin: bases 5657-6113

```
         10         20         30         40         50         60
GCGCGCGTTG ACATTGATTA TTGACTAGTT ATTAATAGTA ATCAATTACG GGGTCATTAG
CGCGGCGCAAC TGTAACTAAT AACTGATCAA TAATTATCAT TAGTTAATGC CCCAGTAATC
         70         80         90        100        110        120
TTCATAGCCC ATATATGGAG TTCCGCGTTA CATAACTTAC GGTAAATGGC CCGCCTGGCT
AAGTATCGGG TATATACCTC AAGGGCGCAAT GTATTGAATG CCATTTACCG GGCGGACCGA
        130        140        150        160        170        180
GACCGCCCAA CGACCCCCGC CCATTGACGT CAATAATGAC GTATGTTCCC ATAGTAACGC
CTGGCGGGTT GCTGGGGGCG GGTAACTGCA GTTATTACTG CATACAAGGG TATCATTGCG
```

```
         190        200        210        220        230        240
CAATAGGAC  TTTCCATTGA CGTCAATGGG TGGACTATTT ACGGTAAACT GCCCACTTGG
GTTATCCCTG AAAGGTAACT GCAGTTACCC ACCTGATAAA TGCCATTTGA CGGGTGAACC 250        260        270        280        290        300
CAGTACATCA AGTGTATCAT ATGCCAAGTA CGCCCCCTAT TGACGTCAAT GACGGTAAAT
GTCATGTAGT TCACATAGTA TACGGTTCAT GCGGGGGATA ACTGCAGTTA CTGCCATTTA 310        320        330        340        350        360
GGCCCGCCTG GCATTATGCC CAGTACATGA CCTTATGGGA CTTTCCTACT TGGCAGTACA
CCGGGCGGAC CGTAATACGG GTCATGTACT GGAATACCCT GAAAGGATGA ACCGTCATGT 370        380        390        400        410        420
TCTACGTATT AGTCATCGCT ATTACCATGG TGATGCGGTT TTGGCAGTAC ATCAATGGGC
AGATGCATAA TCAGTAGCGA TAATGGTACC ACTACGCCAA AACCGTCATG TAGTTACCCG 430        440        450        460        470        480
GTGGATAGCG GTTTGACTCA CGGGGATTTC CAAGTCTCCA CCCCATTGAC GTCAATGGGA
CACCTATCGC CAAACTGAGT GCCCCTAAAG GTTCAGAGGT GGGGTAACTG CAGTTACCCT 490        500        510        520        530        540
GTTTGTTTTG GCACCAAAAT CAACGGGACT TTCCAAAATG TCGTAACAAC TCCGCCCCAT
CAAACAAAAC CGTGGTTTTA GTTGCCCTGA AAGGTTTTAC AGCATTGTTG AGGCGGGGTA 550        560        570        580        590        600
TGACGCAAAT GGGCGGTAGG CGTGTACGGT GGGAGGTCTA TATAAGCAGA GCTCTCTGGC
ACTGCGTTTA CCCGCCATCC GCACATGCCA CCCTCCAGAT ATATTCGTCT CGAGAGACCG 610        620        630        640        650        660
```

FIG. 6B

```
TAACTAGAGA ACCCACTGCT TACTGGCTTA TCGAAATTAA TACGACTCAC TATAGGGAGA
ATTGATCTCT TGGGTGACGA ATGACCGAAT AGCTTTAATT ATGCTGAGTG ATATCCCTCT
                     670        680        690        700        710        720
CCCAAGCTTG GTACCGAGCT CGGATCCACT AGTAACGGCC GCCAGTGTGC TGGAATTCGG
GGGTTCGAAC CATGGCTCGA GCCTAGGTGA TCATTGCCGG CGGTCACACG ACCTTAAGCC
                     730        740        750        760        770        780
CTTGGGATA TCCACCATGG AGACAGACAC ACTCCTGCTA TGGGTACTGC TGCTCTGGT
GAACCCTAT AGGTGGTACC TCTGTCTGTG TGAGGACGAT ACCCATGACG ACGAGACCA
                     790        800        810        820        830        840
TCCAGGTTCC ACTGGTGACT ATCCATATGA TGTTCCAGAT TATGCTGGGC CCCAGCCGGC
AGGTCCAAGG TGACCACTGA TAGGTATACT ACAAGGTCTA ATACGACCCG GGGTCGGCCG
                     850        860        870        880        890        900
CATGGCCGAG GTCAAGCTGC AGGAGTCAGG GGGAGGCTTA GTGCAGCCTG GAGGGTCCCG
GTACCGGCTC CAGTTCGACG TCCTCAGTCC CCCTCCGAAT CACGTCGGAC CTCCCAGGGC
                     910        920        930        940        950        960
GAAACTCTCC TGTGCAGCCT CTGGATTCAC TTTCAGTAGC TTTGGAATGC ACTGGGTTCG
CTTTGAGAGG ACACGTCGGA GACCTAAGTG AAAGTCATCG AAACCTTACG TGACCCAAGC
                     970        980        990       1000       1010       1020
TCAGGCTCCA GAGAAGGGGC TGGAGTGGGT CGCATATATT AGTAGTGGCA GTAGTACCAT
AGTCCGAGGT CTCTTCCCCG ACCTCACCCA GCGTATATAA TCATCACCGT CATCATGGTA
                    1030       1040       1050       1060       1070       1080
CTACTATGCA GACACAGTGA AGGGACGATT CACCATCTCC AGAGACAATC CAAGAACAC
GATGATACGT CTGTGTCACT TCCCTGCTAA GTGGTAGAGG TCTCTGTTAG GGTTCTTGTG
```

FIG. 6C

```
1090       1100       1110       1120       1130       1140
CCTGTCCTG  CAAATGACCA GTCTAAGGTC TGAGACACG  GNCATGTATT ACTGTGCAAG
GGACAAGGAC GTTTACTGGT CAGATTCCAG ACTCCTGTGC CNGTACATAA TGACACGTTC 1150       1160       1170       1180       1190       1200
AGATTACGGG GCTTATTGGG GCCAAGGGAC CACGGNCACC GTCTCCTCAG GTGGAGGCGG
TCTAATGCCC CGAATAACCC CGGTTCCCTG GTGCCNGTGG CAGAGGAGTC CACCTCCGCC 1210       1220       1230       1240       1250       1260
CTCAGGCGGA GGTGGCTCTG GCGGTGGCGG ATCGGACATT GAGCTCACCC AGTCTCCAGC
GAGTCCGCCT CCACCGAGAC CGCCACCGCC TAGCCTGTAA CTCGAGTGGG TCAGAGGTCG 1270       1280       1290       1300       1310       1320
AATCATGTCT GCATCTCCAG GGGAGAGGGT CACCATGACC TGCAGTGCCA GTTCAAGTGT
TTAGTACAGA CGTAGAGGTC CCCTCTCCCA GTGGTACTGG ACGTCACGGT CAAGTTCACA 1330       1340       1350       1360       1370       1380
AAGGTACATG AACTGGTTCC AACAGAAGTC AGGCACCTCC CCCAAAAGAT GGATTTATGA
TTCCATGTAC TTGACCAAGG TTGTCTTCAG TCCGTGGAGG GGGTTTTCTA CCTAAATACT 1390       1400       1410       1420       1430       1440
CACATCCAAA CTGTCTTCTG GAGTCCCTGC TCGCTTCAGT GGCAGTGGGT CTGGGACCTC
GTGTAGGTTT GACAGAAGAC CTCAGGGACG AGCGAAGTCA CCGTCACCCA GACCCTGGAG 1450       1460       1470       1480       1490       1500
TTACTCTCTC ACAATCAGCA GCATGGAGGC TGAAGATGCT GCCACTTACT ACTGCCAGCA
AATGAGAGAG TGTTAGTCGT CGTACCTCCG ACTTCTACGA CGGTGAATGA TGACGGTCGT 1510       1520       1530       1540       1550       1560
GTGGAGTAGT AACCCACTCA CGTTCGGTGC TGGGACCAAG CTGGAGCTGA AACGG---GC
CACCTCATCA TTGGGTGAGT GCAAGCCACG ACCCTGGTTC GACCTCGACT TTGCC---CG
```

FIG. 6D

| 1570 | 1580 | 1590 | 1600 | 1610 | 1620 |
|---|---|---|---|---|---|
| GGCCGCAGAA | CAAAAACTCA | TCTCAGAAGA | GGATCTGAAT | GGGGCCGTCG | ACGAACAAAA |
| CCGGCGTCTT | GTTTTTGAGT | AGAGTCTTCT | CCTAGACTTA | CCCCGGCAGC | TGCTTGTTTT |

| 1630 | 1640 | 1650 | 1660 | 1670 | 1680 |
|---|---|---|---|---|---|
| ACTCATCTCA | GAAGAGGATC | TGAATGCTGT | GGGCCAGGAC | ACGCAGGAGG | TCATCGTGGT |
| TGAGTAGAGT | CTTCTCCTAG | ACTTACGACA | CCCGGTCCTG | TGCCGTCCTCC | AGTAGCACCA |

| 1690 | 1700 | 1710 | 1720 | 1730 | 1740 |
|---|---|---|---|---|---|
| GCCACACTCC | TTGCCCTTTA | AGTGGTGT | GATCTCAGCC | ATCCTGGCCC | TGGTGGTGCT |
| CGGTGTGAGG | AACGGGAAAT | TCCACCACCA | CTAGAGTCGG | TAGGACCGGG | ACCACCACGA |

| 1750 | 1760 | 1770 | 1780 | 1790 | 1800 |
|---|---|---|---|---|---|
| CACCATCATC | TCCCTTATCA | TCCCTCATCAT | GCTTTGGCAG | AAGAAGCCAC | GTTAGGCGGC |
| GTGGTAGTAG | AGGGAATAGT | AGGAGTAGTA | CGAAACCGTC | TTCTTCGGTG | CAATCCGCCG |

| 1810 | 1820 | 1830 | 1840 | 1850 | 1860 |
|---|---|---|---|---|---|
| CGCTCGAGCA | TGCATCTAGA | GGGCCCTATT | CTATAGTGTC | ACCTAAATGC | TAGAGCTCGC |
| GCGAGCTCGT | ACGTAGATCT | CCCGGGATAA | GATATCACAG | TGGATTTACG | ATCTCGAGCG |

| 1870 | 1880 | 1890 | 1900 | 1910 | 1920 |
|---|---|---|---|---|---|
| TGATCAGCCT | CGACTGTGCC | TTCTAGTTGC | CAGCCATCTG | TTGTTTGCCC | CTCCCCCGTG |
| ACTAGTCGGA | GCTGACACGG | AAGATCAACG | GTCGGTAGAC | AACAAACGGG | GAGGGGGCAC |

| 1930 | 1940 | 1950 | 1960 | 1970 | 1980 |
|---|---|---|---|---|---|
| CCTTCCTTGA | CCCTGGAAGG | TGCCACTCCC | ACTGTCCTTT | CCTAATAAAA | TGAGGAAATT |
| GGAAGGAACT | GGGACCTTCC | ACGGTGAGGG | TGACAGGAAA | GGATTATTTT | ACTCCTTTAA |

| 1990 | 2000 | 2010 | 2020 | 2030 | 2040 |
|---|---|---|---|---|---|
| GCATCGCATT | GTCTGAGTAG | ATTCTGGGGG | GTGGGGTGGG | GCAGGACAGC |  |
| CGTAGCGTAA | CAGACTCATC | TAAGACCCCC | CACCCCACCC | CGTCCTGTCG |  |

FIG. 6E

```
2050       2060       2070       2080       2090       2100
AAGGGGGAGG ATTGGAAGA  CAATAGCAGG CATGCTGGGG ATGCGGTGGG CTCTATGGCT
TTCCCCCTCC TAACCCTTCT GTTATCGTCC GTACGACCCC TACGCCACCC GAGATACCGA 2110       2120       2130       2140       2150       2160
TCTGAGGCGG AAAGAACCAG TGGCGGTAAT ACGGTTATCC ACAGAATCAG GGGATAACGC
AGACTCCGCC TTTCTTGGTC ACCGCCATTA TGCCAATAGG TGTCTTAGTC CCCTATTGCG 2170       2180       2190       2200       2210       2220
AGGAAAGAAC ATGTGAGCAA AAGGCCAGCA AAAGGCCAGG AACCGTAAAA AGGCCGCGTT
TCCTTTCTTG TACACTCGTT TTCCGGTCGT TTTCCGGTCC TTGGCATTTT TCCGGCGCAA 2230       2240       2250       2260       2270       2280
GCTGGCGTTT TTCCATAGGC TCCGCCCCCC TGACGAGCAT CACAAAAATC GACGCTCAAG
CGACCGCAAA AAGGTATCCG AGGCGGGGGG ACTGCTCGTA GTGTTTTTAG CTGCGAGTTC 2290       2300       2310       2320       2330       2340
TCAGAGGTGG CGAAACCCGA CAGGACTATA AAGATACCAG GCGTTTCCCC CTGGAAGCTC
AGTCTCCACC GCTTTGGGCT GTCCTGATAT TTCTATGGTC CGCAAAGGGG GACCTTCGAG 2350       2360       2370       2380       2390       2400
CCTCGTGCGC TCTCCTGTTC CGACCCTGCC GCTTACCGGA TACCTGTCCG CCTTTCTCCC
GGAGCACGCG AGAGGACAAG GCTGGGACGG CGAATGGCCT ATGGACAGGC GGAAAGAGGG 2410       2420       2430       2440       2450       2460
TTCGGGAAGC GTGGCGCTTT CTCATAGCTC ACGCTGTAGG TATCTCAGTT CGGTGTAGGT
AAGCCCTTCG CACCGCGAAA GAGTATCGAG TGCGACATCC ATAGAGTCAA GCCACATCCA 2470       2480       2490       2500       2510       2520
CGTTCGCTCC AAGCTGGGCT GTGTGCACGA ACCCCCCGTT CAGCCCGACC GCTGCGCCTT
GCAAGCGAGG TTCGACCCGA CACACGTGCT TGGGGGGCAA GTCGGGCTGG CGACGCGGAA
```

FIG. 6F

```
      2530           2540           2550           2560           2570           2580
ATCCGGTAAC    TATCGTCTTG    AGTCCAACCC    GGTAAGACAC    GACTTATCGC    CACTGGCAGC
TAGGCCATTG    ATAGCAGAAC    TCAGGTTGGG    CCATTCTGTG    CTGAATAGCG    GTGACCGTCG 2590           2600           2610           2620           2630           2640
AGCCACTGGT    AACAGGATTA    GCAGAGCGAG    GTATGTAGGC    GGTGCTACAG    AGTTCTTGAA
TCGGTGACCA    TTGTCCTAAT    CGTCTCGCTC    CATACATCCG    CCACGATGTC    TCAAGAACTT 2650           2660           2670           2680           2690           2700
GTGGTGGCCT    AACTACGGCT    ACACTAGAAG    GACAGTATTT    GGTATCTGCG    CTCTGCTGAA
CACCACCGGA    TTGATGCCGA    TGTGATCTTC    CTGTCATAAA    CCATAGACGC    GAGACGACTT 2710           2720           2730           2740           2750           2760
GCCAGTTACC    TTCGGAAAAA    GAGTTGGTAG    CTCTTGATCC    GGCAAACAAA    CCACCGCTGG
CGGTCAATGG    AAGCCTTTTT    CTCAACCATC    GAGAACTAGG    CCGTTTGTTT    GGTGGCGACC 2770           2780           2790           2800           2810           2820
TAGCGGTGGT    TTTTTGTTT    GCAAGCAGCA    GATTACGCGC    AGAAAAAAAG    GATCTCAAGA
ATCGCCACCA    AAAAAACAAA    CGTTCGTCGT    CTAATGCGCG    TCTTTTTTTC    CTAGAGTTCT 2830           2840           2850           2860           2870           2880
AGATCCTTTG    ATCTTTTCTA    CGGGGTCTGA    CGCTCAGTGG    AACGAAAACT    CACGTTAAGG
TCTAGGAAAC    TAGAAAAGAT    GCCCCAGACT    GCGAGTCACC    TTGCTTTTGA    GTGCAATTCC 2890           2900           2910           2920           2930           2940
GATTTTGGTC    ATGAGATTAT    CAAAAAGGAT    CTTCACCTAG    ATCCTTTTAA    ATTAAAAATG
CTAAAACCAG    TACTCTAATA    GTTTTTCCTA    GAAGTGGATC    TAGGAAAATT    TAATTTTTAC 2950           2960           2970           2980           2990           3000
AAGTTTTAAA    TCAATCTAAA    GTATATATGA    GTAACCTGAG    GCTATGGCAG    GGCCTGCCGC
TTCAAAATTT    AGTTAGATTT    CATATATACT    CATTGGACTC    CGATACCGTC    CCGGACGGCG
```

FIG. 6G

```
3010        3020        3030        3040        3050        3060
CCCGACGTTG  GCTGCGAGCC  CTGGGCCTTC  ACCCGAACTT  GGGGGGTGGG  GTGGGAAAA
GGGCTGCAAC  CGACGCTCGG  GACCCGGAAG  TGGGCTTGAA  CCCCCACCC   CACCCCTTTT 3070        3080        3090        3100        3110        3120
GGAAGAAACG  CGGGCGTATT  GGCCCCAATG  GGGTCTCGGT  GGGGTATCGA  CAGAGTGCCA
CCTTCTTTGC  GCCCGCATAA  CCGGGGTTAC  CCCAGAGCCA  CCCCATAGCT  GTCTCACGGT 3130        3140        3150        3160        3170        3180
GCCCTGGGAC  CGAACCCCGC  GTTTATGAAC  AAACGACCCA  ACACCGTGCG  TTTTATTCTG
CGGGACCCTG  GCTTGGGGCG  CAAATACTTG  TTTGCTGGGT  TGTGGCACGC  AAAATAAGAC 3190        3200        3210        3220        3230        3240
TCTTTTATT   GCCGTCATAG  CGCGGGTTCC  TTCCGGTATT  GTCTCCTTCC  GTGTTTCAGT
AGAAAAATAA  CGGCAGTATC  GCGCCCAAGG  AAGGCCATAA  CAGAGGAAGG  CACAAAGTCA 3250        3260        3270        3280        3290        3300
TAGCCTCCCC  CTAGGGTGGG  CGAAGAACTC  CAGCATGAGA  TCCCCGCGCT  GGAGGATCAT
ATCGGAGGGG  GATCCCACCC  GCTTCTTGAG  GTCGTACTCT  AGGGGCGCGA  CCTCCTAGTA 3310        3320        3330        3340        3350        3360
CCAGCCGGCG  TCCCGGAAAA  CGATTCCGAA  GCCCAACCTT  TCATAGAAGG  CGGCGGTGGA
GGTCGGCCGC  AGGGCCTTTT  GCTAAGGCTT  CGGGTTGGAA  AGTATCTTCC  GCCGCCACCT 3370        3380        3390        3400        3410        3420
ATCGAAATCT  CGTGATGGCA  GGTTGGGCGT  CGCTTGGTCG  GTCATTTCGA  ACCCAGAGT
TAGCTTTAGA  GCACTACCGT  CCAACCCGCA  GCGAACCAGC  CAGTAAAGCT  TGGGTCTCA 3430        3440        3450        3460        3470        3480
CCCGCTCAGA  AGAACTCGTC  AAGAAGGCGA  TAGAAGGCGA  TGCCGCTGGA  ATCGGGAGCG
                                                TACGGCGACCT AGCCCTCGC
```

```
         3490       3500       3510       3520       3530       3540
GGGCGAGTCT TCTTGAGCAG TTCTTCCGCT ATCTTCCGCT ACGCGACGCT TAGCCCTGCC
GCGATACCGT AAAGCACGAG GAAGCGGTCA GCCCATTCGC CGCCAAGCTC TTCAGCAATA
CGCTATGGCA TTTCGTGCTC CTTCGCCAGT CGGGTAAGCG GCGGTTCGAG AAGTCGTTAT 3550       3560       3570       3580       3590       3600
TCACGGGTAG CCAACGCTAT GTCCTGATAG CGGTCCGCCA CACCCAGCCG GCCACAGTCG
AGTGCCCATC GGTTGCGATA CAGGACTATC GCCAGGCGGT GTGGGTCGGC CGGTGTCAGC 3610       3620       3630       3640       3650       3660
ATGAATCCAG AAAAGCGGCC ATTTTCCACC ATGATATTCG GCAAGCAGGC ATGGCCATGG
TACTTAGGTC TTTTCGCCGG TAAAAGGTGG TACTATAAGC CGTTCGTCCG TAGGCGTACC 3670       3680       3690       3700       3710       3720
GTCACGACGA GATCCTCGCC GTCGGGCATG CTCGCCTTGA GCCTGGCCTC CAGTTCGCGT
CAGTGCTGCT CTAGGAGCGG CAGCCCGTAC GAGCGGAACT CGGACCGCTT GTCAAGCCGA 3730       3740       3750       3760       3770       3780
GGGCGGAGCC CCTGATGATC TTTGATCATCC TGATCGACAA GCCAGGCTTC CATCCGAGTA
CCCGCCTCGG GGACTACGAG AAACTAGTAGG ACTAGCTGTT CGGTCCGAAG GTAGGCTCAT 3790       3800       3810       3820       3830       3840
CGTGCTCGCT CGATGCGATG TTTCGCTTGG TGGTCGAATG GGCAGGTAGC CGGATCAAGC
GCACGAGCGA GCTACGCTAC AAAGCGAACC ACCAGCTTAC CCGTCCATCG GCCTAGTTCG 3850       3860       3870       3880       3890       3900
GTATGCAGCC GCCGCATTGC ATCAGCCATG ATGGATACTT TCTCGGCAGG AGCAAGGTGA
CATACGTCGG CGGCGTAACG TAGTCGGTAC TACCTATGAA AGAGCCGTCC TCGTTCCACT
```

```
       3910       3920       3930       3940       3950       3960
GATGACAGGA GATCCTGCCC CGGCACTTCG CCCAATAGCA GCCAGTCCCT TCCCGCTTCA
CTACTGTCCT CTAGGACGGG GCCGTGAAGC GGGTTATCGT CGGTCAGGGA AGGGCGAAGT 3970       3980       3990       4000       4010       4020
GTGACAACGT CGAGCACAGC TGCGCAAGGA ACGCCCGTCG TGGCCAGCCA CGATAGCCGC
CACTGTTGCA GCTCGTGTCG ACGGGTTCCT TGCGGGCAGC ACCGGTCGGT GCTATCGGCG 4030       4040       4050       4060       4070       4080
GCTGCCTCGT CTTGCAGTTC ATTCAGGGCA CCGGACAGGT CGGTCTTGAC AAAAAGAACC
CGACGGAGCA GAACGTCAAG TAAGTCCCGT GGCCTGTCCA GCCAGAACTG TTTTTCTTGG 4090       4100       4110       4120       4130       4140
GGGCGCCCCT GCGCTGACAG CCGGAACACG GCGGCATCAG AGCAGCCGAT TGTCTGTTGT
CCCGCGGGGA CGCGACTGTC GGCCTTGTGC CGCCGTAGTC TCGTCGGCTA ACAGACAACA 4150       4160       4170       4180       4190       4200
GCCCAGTCAT AGCCGAATAG CCTCTCCACC CAAGCGGCCG GAGAACCTGC GTGCAATCCA
CGGGTCAGTA TCGGCTTATC GGAGAGGTGG GTTCGCCGGC CTCTTGGACG CACGTTAGGT 4210       4220       4230       4240       4250       4260
TCTTGTTCAA TCATGCGAAA CGATCCTCAT CCTGTCTCTT GATCGATCTT TGCAAAAGCC
AGAACAAGTT AGTACGCTTT GCTAGGAGTA GGACAGAGAA CTAGCTAGAA ACGTTTTCGG 4270       4280       4290       4300       4310       4320
TAGGCCTCCA AAAAAGCCTC CTCACTACTT CTGGAATAGC TCAGAGGCCG AGGCGGCCTC
ATCCGGAGGT TTTTTCGGAG GAGTGATGAA GACCTTATCG AGTCTCCGGC TCCGCCGGAG 4330       4340       4350       4360       4370       4380
GGCCCTCTGCA TAAATAAAAA AAATTAGTCA GCCATGGGGC GGAGAATGGG CGGAACTGGG
CCGGAGACGT ATTTATTTTT TTTAATCAGT CGGTACCCCG CCTCTTACCC GCCTTGACCC 4390       4400       4410       4420       4430       4440
```

FIG. 6J

```
CGGAGTTAGG GGCGGGATGG GCGGAGTTAG GGGCGGGACT ATGGTTGCTG ACTAATTGAG
GCCTCAATCC CGGCCCTACC CGCCTCAATC CCCGCCCTGA TACCAACGAC TGATTAACTC
     4450       4460       4470       4480       4490       4500

ATGCATGCTT TGCATACTTC TGCCTGCTGG GGAGCCTGGG GACTTTCCAC ACCTGGTTGC
TACGTACGAA ACGTATGAAG ACGGACGACC CCTCGGACCC CTGAAAGGTG TGGACCAACG
     4510       4520       4530       4540       4550       4560

TGACTAATTG AGATGCATGC TTTGCATACT TCTGCCTGCT GGGGAGCCTG GGGACTTTCC
ACTGATTAAC TCTACGTACG AAACGTATGA AGACGGACGA CCCCTCGGAC CCCTGAAAGG
     4510       4520       4530       4540       4550       4560

ACACCCTAAC TGACACACAT TCCACAGCTG GTTCTTTCCG CCTCAGGACT CTTCCTTTTT
TGTGGGATTG ACTGTGTGTA AGGTGTCGAC CAAGAAAGGC GGAGTCCTGA GAAGGAAAAA
     4570       4580       4590       4600       4610       4620

CAATAAATCA ATCTAAAGTA TATATGAGTA AACTTGGTCT GACAGTTACC AATGCTTAAT
GTTATTTAGT TAGATTTCAT ATATACTCAT TTGAACCAGA CTGTCAATGG TTACGAATTA
     4630       4640       4650       4660       4670       4680

CAGTGAGGCA CCTATCTCAG CGATCTGTCT ATTTCGTTCA TCCATAGTTG CCTGACTCCC
GTCACTCCGT GGATAGAGTC GCTAGACAGA TAAAGCAAGT AGGTATCAAC GGACTGAGGG
     4690       4700       4710       4720       4730       4740

CGTCGTGTAG ATAACTACGA TACGGGAGGG CTTACCATCT GGCCCCAGTG CTGCAATGAT
GCAGCACATC TATTGATGCT ATGCCCTCCC GAATGGTAGA CCGGGGTCAC GACGTTACTA
     4750       4760       4770       4780       4790       4800

ACCGCGAGAC CCACGCTCAC CGGCTCCAGA TTTATCAGCA ATAAACCAGC CAGCCGGAAG
TGGCGCTCTG GGTGCGAGTG GCCGAGGTCT AAATAGTCGT TATTTGGTCG GTCGGCCTTC
     4810       4820       4830       4840       4850       4860
```

FIG. 6K

```
     4870        4880       4890       4900       4910       4920
GGCCGAGCGC AGAAGTGGTC CTGCAACTTT ATCCGCCTCC ATCCAGTCTA TTAATGTTG
CCGGCTCGCG TCTTCACCAG GACGTTGAAA TAGGCGGAGG TAGGTCAGAT AATTAACAAC 4930        4940       4950       4960       4970       4980
CCGGAAGCT AGAGTAAGTA GTTCGCCAGT TAATAGTTTG CGCAACGTTG TTGCCATTGC
GGCCCTTCGA TCTCATTCAT CAAGCGGTCA ATTATCAAAC GCGTTGCAAC AACGGTAACG 4990        5000       5010       5020       5030       5040
TACAGGCATC GTGGTGTCAC GCTCGTCGTT TGGTATGGCT TCATTCAGCT CCGGTTCCCA
ATGTCCGTAG CACCACAGTG CGAGCAGCAA ACCATACCGA AGTAAGTCGA GGCCAAGGGT 5050        5060       5070       5080       5090       5100
ACGATCAAGG CGAGTTACAT GATCCCCCAT GTTGTGCAAA AAAGCGGTTA GCTCCTTCGG
TGCTAGTTCC GCTCAATGTA CTAGGGGGTA CAACACGTTT TTTCGCCAAT CGAGGAAGCC 5110        5120       5130       5140       5150       5160
TCCTCCGATC GTTGTCAGAA GTAAGTTGGC CGCAGTGTTA TCACTCATGG TTATGGCAGC
AGGAGGCTAG CAACAGTCTT CATTCAACCG GCGTCACAAT AGTGAGTACC AATACCGTCG 5170        5180       5190       5200       5210       5220
ACTGCATAAT TCTCTTACTG TCATGCCATC CGTAAGATGC TTTTTCTGTGA CTGGTGAGTA
TGACGTATTA AGAGAATGAC AGTACGGTAG GCATTCTACG AAAAGACACT GACCACTCAT 5230        5240       5250       5260       5270       5280
CTCAACCAAG TCATTCTGAG AATAGTGTAT GCGGGGACCG AGTTGCTCTT GCCCGGCGTC
GAGTTGGTTC AGTAAGACTC TTATCACATA CGCCCCTGGC TCAACGAGAA CGGGCCGCAG 5290        5300       5310       5320       5330       5340
AATACGGGAT AATACCGCGC CACATAGCAG AACTTTAAAA GTGCTCATCA TTGGAAAACG
TTATGCCCTA TTATGGCGCG GTGTATCGTC TTGAAATTTT CACGAGTAGT AACCTTTTGC
```

```
       5350       5360       5370       5380       5390       5400
 TTCTTCGGGG CGAAAACTCT CAAGGATCTT ACCGCTGTTG AGATCCAGTT CGATGTAACC
 AAGAAGCCCC GCTTTTGAGA GTTCCTAGAA TGGCGACAAC TCTAGGTCAA GCTACATTGG 5410       5420       5430       5440       5450       5460
 CACTCGTGCA CCCAACTGAT CTTCAGCATC TTTTACTTTC ACCAGCGTTT CTGGGTGAGC
 GTGAGCACGT GGGTTGACTA GAAGTCGTAG AAAATGAAAG TGGTCGCAAA GACCCACTCG 5470       5480       5490       5500       5510       5520
 AAAAACAGGA AGGCAAAATG CCGCAAAAAA GGGAATAAGG GCGACACGGA AATGTTGAAT
 TTTTTGTCCT TCCGTTTTAC GGCGTTTTTT CCCTTATTCC CGCTGTGCCT TTACAACTTA 5530       5540       5550       5560       5570       5580
 ACTCATACTC TTCCTTTTTC AATATTATTG AAGCATTTAT CAGGGTTATT GTCTCATGAG
 TGAGTATGAG AAGGAAAAAG TTATAATAAC TTCGTAAATA GTCCCAATAA CAGAGTACTC 5590       5600       5610       5620       5630       5640
 CGGATACATA TTTGAATGTA TTTAGAAAAA TAAACAAATA GGGGTTCCGC GCACATTTCC
 GCCTATGTAT AAACTTACAT AAATCTTTTT ATTTGTTTAT CCCCAAGGCG CGTGTAAAGG 5650       5660       5670       5680       5690       5700
 CCGAAAAGTG CCACCTGACG CGCCCTGTAG CGGGCCATTA AGCGGGGCGG GTGTGGTGGT
 GGCTTTTCAC GGTGGACTGC GCGGGACATC GCCCGGTAAT TCGCCCCGCC CACACCACCA
```

FIG. 6N

```
          5710       5720       5730       5740       5750       5760
    TACGGCGAGC GTGACCGCTA CACTTGCCAG CGCCCTAGCG CCCGCTCCTT TCGCTTTCTT
    ATGCGCTCG CACTGGCGAT GTGAACGGTC GCGGGATCGC GGGCGAGGAA AGCGAAAGAA 5770       5780       5790       5800       5810       5820
    CCCTTCCTTT CTCGCCACGT TCGCCGGCTT TCCCCGTCAA GCTCTAAATC GGGGGCTCCC
    GGGAAGGAAA GAGCGGTGCA AGCGGCCGAA AGGGGCAGTT CGAGATTTAG CCCCCGAGGG 5830       5840       5850       5860       5870       5880
    TTTAGGGTTC CGATTTAGTG CTTTACGGCA CCTCGACCCC AAAAAACTTG ATTAGGGTGA
    AAATCCCAAG GCTAAATCAC GAAATGCCGT GGAGCTGGGG TTTTTTGAAC TAATCCCACT 5890       5900       5910       5920       5930       5940
    TGGTTCACGT AGTGGGCCAT CGCCCTGATA GACGGTTTTT CGCCCTTTGA CGTTGAGTC
    ACCAAGTGCA TCACCCGGTA GCGGGACTAT CTGCCAAAAA GCGGGAAACT GCAACCTCAG 5950       5960       5970       5980       5990       6000
    CACGTTCTTT AATAGTGGAC TCTTGTTCCA AACTGGAACA ACACTCAACC CTATCTCGGT
    GTGCAAGAAA TTATCACCTG AGAACAAGGT TTGACCTTGT TGTGAGTTGG GATAGAGCCA 6010       6020       6030       6040       6050       6060
    CTATTCTTTT GATTTATAAG GGATTTTGCC GATTTCGGCC TATTGGTTAA AAAATGAGCT
    GATAAGAAAA CTAAATATTC CCTAAAACGG CTAAAGCCGG ATAACCAATT TTTTACTCGA 6070       6080       6090       6100       6110       6120
    GATTAACAA AAATTTAACG CGAATTTTAA CAAAATATTA ACGCTTACAA TTTAC......
    CTAAATTGTT TTTAAATTGC GCTTAAAATT GTTTTATAAT TGCGAATGTT AAATG......
```

CMV (1-596), T7 (638-657), MCS (664-718), LacZ (728-3787*)
MCS (3791-3847) Kan (6235-5447) Amp (7547-6687)
*NOTE: 3' sequence of LacZ may not be exact)

```
         10         20         30         40         50         60
GCGGCGGGTTG ACATTGATTA TTGACTAGTT ATTAATAGTA ATCAATTACG GGGTCATTAG
         70         80         90        100        110        120
TTCATAGCCC ATATATGGAG TTCCGCGTTA CATAACTTAC GGTAAATGGC CCGCCTGGCT
        130        140        150        160        170        180
GACCGCCCAA CGACCCCCGC CCATTGACGT CAATAATGAC GTATGTTCCC ATAGTAACGC
        190        200        210        220        230        240
CAATAGGGAC TTTCCATTGA CGTCAATGGG TGGACTATTT ACGGTAAACT GCCCACTTGG
        250        260        270        280        290        300
CAGTACATCA AGTGTATCAT ATGCCAAGTA CGCCCCCTAT TGACGTCAAT GACGGTAAAT
        310        320        330        340        350        360
GGCCCGCCTG GCATTATGCC CAGTACATGA CCTTATGGGA CTTTCCTACT TGGCAGTACA
        370        380        390        400        410        420
TCTACGTATT AGTCATCGCT ATTACCATGG TGATGCGGTT TTGGCAGTAC ATCAATGGGC
```

FIG. 7B

```
        430        440        450        460        470        480
GTGGATAGCG GTTTGACTCA CGGGGATTTC CAAGTCTCCA CCCCATTGAC GTCAATGGGA 490        500        510        520        530        540
GTTTGTTTTG GCACCAAAAT CAACGGGACT TTCCAAAATG TCGTAACAAC TCCGCCCCAT 550        560        570        580        590        600
TGACGCAAAT GGGCGGTAGG CGTGTACGGT GGGAGGTCTA TATAAGCAGA GCTCTCTGGC 610        620        630        640        650        660
TAACTAGAGA ACCCACTGCT TACTGGCTTA TCGAAATTAA TACGACTCAC TATAGGGAGA 670        680        690        700        710        720
CCCAAGCTTG GTACCGAGCT CGGATCCACT AGTAACGGCC GCCAGTGTGC TGGAATTCGG 730        740        750        760        770        780
CTTATTCATG ATAGATCCCG TCGTTTTACA ACGTCGTGAC TGGGAAAACC CTGGCGTTAC 790        800        810        820        830        840
CCAACTTAAT CGCCTTGCAG CACATCCCCC TTTCGCCAGC TGGCGTAATA GCGAAGAGGC 850        860        870        880        890        900
CCGCACCGAT CGCCCTTCCC AACAGTTGCG CAGCCTGAAT GGCGAATGGC GCTTTGCCTG
```

FIG. 7C

```
         910        920        930        940        950        960
GTTTCCGGTA CCAGAAGCGG TGCCGGAAAG CTGGCTGGAG TGCGGATCTTC CTGAGGCCGA 970        980        990       1000       1010       1020
TACTGTCGTC GTCCCCTCAA ACTGGCAGAT GCACGGTTAC GATGCGCCCA TCTACACCAA 1030       1040       1050       1060       1070       1080
CGTAACCTAT CCCATTACGG TCAATCCGCC GTTTGTTCCC ACGGAGAATC CGACGGGTTG 1090       1100       1110       1120       1130       1140
TTACTCGCTC ACATTTAATG TTGATGAAAG CTGGCTACAG GAAGGCCAGA CCGGAATTAT 1150       1160       1170       1180       1190       1200
TTTTGATGGC GTTAACTCGG CGTTTCATCT GTGGTGCAAC GGGGCGCTGGG TCGGTTACGG 1210       1220       1230       1240       1250       1260
CCAGGACAGT CGTTTGCCGT CTGAATTTGA CCTGAGCGCA TTTTTACGCG CCCGGAGAAAA 1270       1280       1290       1300       1310       1320
CCGCCTCGCG GTGATGGTGC TGCGGTTGGAG TGACGGCAGT TATCTGGAAG ATCAGGATAT 1330       1340       1350       1360       1370       1380
GTGGCGGATG AGCGGCATTT TCCGTGACGT CTCGTTGCTG CATAAACCGA CTACACAAAT
```

FIG. 7D

```
     1390        1400       1410       1420       1430       1440
CAGCGATTTC CATGTTGCCA CTCGCTTTAA TGATGATTTC AGCCGCGCTG TACTGGAGGC 1450        1460       1470       1480       1490       1500
TGAAGTTCAG ATGTGCGGCG AGTTGCGTGA CTACCTACGG GTAACAGTTT CTTTATGGCA 1510        1520       1530       1540       1550       1560
GGGTGAAACG CAGGTCGCCA GCGGCACCGC GCCTTTCGGC GGTGAAATTA TCGATGAGCG 1570        1580       1590       1600       1610       1620
TGGTGGTTAT GCCGATCGCG TCACACTACG TCTGAACGTC GAAAACCCGA AACTGTGGAG 1630        1640       1650       1660       1670       1680
CGCCGAAATC CCGAATCTCT ATCGTGCGGT GGTTGAACTG CACACCGCCG ACGGCACGCT 1690        1700       1710       1720       1730       1740
GATTGAAGCA GAAGCCTGCG ATGTCGGTTT CCGCGAGGTG CGGATTGAAA ATGGTCTGCT 1750        1760       1770       1780       1790       1800
GCTGCTGAAC GGCAAGCCGT TGCTGATTCG AGGGCGTAAC CGTCACGAGC ATCATCCTCT 1810        1820       1830       1840       1850       1860
GCATGGTCAG GTCATGGATG AGCAGACGAT GGTGCAGGAT ATCCTGCTGA TGAAGCAGAA
```

FIG. 7E

```
     1870       1880       1890       1900       1910       1920
CAACTTTAAC GCCGTGCGCT GTTCGCATTA TCCGAACCAT CCGCTGTGGT ACACGCTGTG 1930       1940       1950       1960       1970       1980
CGACCGCTAC GGCCTGTATG TGGTGGATGA AGCCAATATT GAAACCCACG GCATGGTGCC 1990       2000       2010       2020       2030       2040
AATGAATCGT CTGACCGATG ATCCGCGCTG GCTACCGGGCG ATGAGCGAAC GCGTAACGCG 2050       2060       2070       2080       2090       2100
AATGGTGCAG CGCGATCGTA ATCACCCGAG TGTGATCATC TGGTCGCTGG GGAATGAATC 2110       2120       2130       2140       2150       2160
AGGCCACGGC GCTAATCACG ACGGCGCTGTA TCGCTGGATC AAATCTGTCG ATCCTTCCCG 2170       2180       2190       2200       2210       2220
CCCGGTGCAG TATGAAGGCG GCGGAGCCGA CACCACGGCC ACCGATATTA TTTGCCCGAT 2230       2240       2250       2260       2270       2280
GTACGCGCGC GTGGATGAAG ACCAGCCCTT CCCGGCTGTG CCGAAATGGT CCATCAAAAA 2290       2300       2310       2320       2330       2340
ATGGCTTTCG CTACCTGGAG AGACGCGCCC GCTGATCCTT TGCGAATACG CCCACGCGAT
```

FIG. 7F

```
      2350       2360       2370       2380       2390       2400
GGGTAACAGT CTTGGGCGGT TCGCTAAATA CTGGCAGGCG TTTCGTCAGT ATCCCCGTTT 2410       2420       2430       2440       2450       2460
ACAGGGCGGC TTCGTCTGGG ACTGGGTGGA TCAGTCGCTG ATTAAATATG ATGAAAACGG 2470       2480       2490       2500       2510       2520
CAACCCGTGG TCGGCTTACG GCGGTGATTT TGGCGATACG CCGAACGATC GCCAGTTCTG 2530       2540       2550       2560       2570       2580
TATGAACGGT CTGGTCTTTG CCGACCGCAC GCCGCATCCA GCGCTGACGG AAGCAAAACA 2590       2600       2610       2620       2630       2640
CCAGCAGCAG TTTTTCCAGT TCCGTTTATC CGGGCAAACC ATCGAAGTGA CCAGCGAATA 2650       2660       2670       2680       2690       2700
CCTGTTCCGT CATAGCGGATA ACGAGCTCCT GCACTGGATG GTGGGCGCTGG ATGGTAAGCC 2710       2720       2730       2740       2750       2760
GCTGGCAAGC GGTGAAGTGC CTCTGGATGT CGCTCCACAA GGTAAACAGT TGATTGAACT 2770       2780       2790       2800       2810       2820
GCCTGAACTA CCGCAGCCCGG AGAGCGCCGG GCAACTCTGG CTCACAGTAC GCGTAGTGCA
```

FIG. 7G

```
2830       2840       2850       2860       2870       2880
ACCGAACGCG ACCGCATGGT CAGAAGCCGG GCACATCAGC GCCTGGCAGC AGTGGGTCT 2890       2900       2910       2920       2930       2940
GGCGGAAAAC CTCAGTGTGA CGCTCCCCGC CGGGTCCCAC GCCATCCCGC ATCTGACCAC 2950       2960       2970       2980       2990       3000
CAGCGAAAATG GATTTTTGCA TCGAGCTGGG TAATAAGCGT TGGCAATTTA ACCGCCAGTC 3010       3020       3030       3040       3050       3060
AGGCTTTCTT TCACAGATGT GGATTGGCGA TAAAAAACAA CTGCTGAGCG CGCTGGCGA 3070       3080       3090       3100       3110       3120
TCAGTTCACC CGTGCACCGC TGGATAACGA CATTGGCGTA AGTGAAGCGA CCCGCATTGA 3130       3140       3150       3160       3170       3180
CCCTAACGCC TGGGTCGAAC GCTGGAAGGC GGCGGGCCAT TACCAGGCCG AAGCAGCGTT 3190       3200       3210       3220       3230       3240
GTTGCAGTGC ACGGCAGATA CACTTGCTGA TGCGGTGCTG ATTACGACCG CTCACGCGTG
```

```
         3250       3260       3270       3280       3290       3300
GCAGCATCAG GGGAAAACCT TATTTATCAG CCGGAAAACC TACCGGATTG ATGGTAGTGG 3310       3320       3330       3340       3350       3360
TCAAATGGCG ATTACCGTTG ATGTTGAAGT GGCGAGCGAT ACACCGCATC CGGCGCGGAT 3370       3380       3390       3400       3410       3420
TGGCCTGAAC TGCCAGCTGG CGCAGGTAGC AGAGCGGGTA AACTGGCTCG GATTAGGGCC 3430       3440       3450       3460       3470       3480
GCAAGAAAAC TATCCCGACC GCCTTACTGC CGCCTGTTTT GACCGCTGGG ATCTGCCATT 3490       3500       3510       3520       3530       3540
GTCAGACATG TATACCCCGT ACGTCTTCCC GAGCGAAAAC GGTCTGCGCT GCGGGACGCG 3550       3560       3570       3580       3590       3600
CGAATTGAAT TATGGCCCAC ACCAGTGGCG CGGCGACTTC CAGTTCAACA TCAGCCGCTA 3610       3620       3630       3640       3650       3660
CAGTCAACAG CAACTGATGG AAAACCAGCCA TCGCCATCTG CTGCCAGCGCGG AAGAAGGCAC 3670       3680       3690       3700       3710       3720
ATGGCTGAAT ATCGACGGTT TCCATATGGG GATTGGTGGC GACGACTCCT GGAGCCCGTC 3730       3740       3750       3760       3770       3780
```

```
AGTATCGGCG GAATTCCAGC TGAGGCCCGG TCGCTACCAT TACCAGTTGG TCTGGTGTCA
      3790       3800       3810       3820       3830       3840
AAAATAAGCC GAATTCTGCA GATATCCATC ACACTGGCGG CCGCTCGAGC ATGCATCTAG
      3850       3860       3870       3880       3890       3900
AGGGCCCTAT TCTATAGTGT CACCTAAATG CTAGAGCTCG CTGATCAGCC TCGACTGTGC
      3910       3920       3930       3940       3950       3960
CTTCTAGTTG CCAGCCATCT GTTGTTTGCC CCTCCCCCGT GCCTTCCTTG ACCCTGGAAG
      3970       3980       3990       4000       4010       4020
GTGCCACTCC CACTGTCCTT TCCTAATAAA ATGAGGAAAT TGCATCGCAT TGTCTGAGTA
      4030       4040       4050       4060       4070       4080
GGTGTCATTC TATTCTGGGG GGTGGGGTGG GGCAGGACAG CAAGGGGGAG GATTGGGAAG
      4090       4100       4110       4120       4130       4140
ACAATAGCAG GCATGCTGGG GATGCGGTGG GCTCTATGGC TTCTGAGGCG GAAAGAACCA
      4150       4160       4170       4180       4190       4200
GTGGCGGTAA TACGGTTATC CACAGAATCA GGGGATAACG CAGGAAAGAA CATGTGAGCA
```

FIG. 7J

```
         4210        4220        4230        4240        4250        4260
AAAGGCCAGC AAAAGGCCAG GAACCGTAAA AAGGCCGCGT TGCTGGCGTT TTTCCATAGG 4270        4280        4290        4300        4310        4320
CTCCGCCCCC CTGACGAGCA TCACAAAAAT CGACGCTCAA GTCAGAGGTG GCGAAACCCG 4330        4340        4350        4360        4370        4380
ACAGGACTAT AAAGATACCA GGCGTTTCCC CCTGGAAGCT CCCTCGTGCG CTCTCCTGTT 4390        4400        4410        4420        4430        4440
CCGACCCTGC CGCTTACCGG ATACCTGTCC GCCTTTCTCC CTTCGGGAAG CGTGGCGCTT 4450        4460        4470        4480        4490        4500
TCTCATAGCT CACGCTGTAG GTATCTCAGT TCGGTGTAGG TCGTTCGCTC CAAGCTGGGC 4510        4520        4530        4540        4550        4560
TGTGTGCACG AACCCCCCGT TCAGCCCGAC CGCTGCGCCT TATCCGGTAA CTATCGTCTT 4570        4580        4590        4600        4610        4620
GAGTCCAACC CGGTAAGACA CGACTTATCG CCACTGGCAG CAGCCACTGG TAACAGGATT 4630        4640        4650        4660        4670        4680
AGCAGAGCGA GGTATGTAGG CGGTGCTACA GAGTTCTTGA AGTGGTGGCC TAACTACGGC
```

FIG. 7K

```
        4690           4700           4710           4720           4730           4740
TACACTAGAA GGACAGTATT TGGTATCTGC GCTCTGCTGA AGCCAGTTAC CTTCGGAAAA 4750           4760           4770           4780           4790           4800
AGAGTTGGTA GCTCTTGATC CGGCAAACAA ACCACCGCTG GTAGCGGTGG TTTTTTTGTT 4810           4820           4830           4840           4850           4860
TGCAAGCAGC AGATTACGCG CAGAAAAAAA GGATCTCAAG AAGATCCTTT GATCTTTTCT 4870           4880           4890           4900           4910           4920
ACGGGGTCTG ACGCTCAGTG GAACGAAAAC TCACGTTAAG GGATTTTGGT CATGAGATTA 4930           4940           4950           4960           4970           4980
TCAAAAAGGA TCTTCACCTA GATCCTTTTA AATTAAAAAT GAAGTTTTAA ATCAATCTAA 4990           5000           5010           5020           5030           5040
AGTATATATG AGTAAACTTGA GGCTATGCA GGGCCTGCCG CCCCGACGTT GGCTGCCAGC 5050           5060           5070           5080           5090           5100
CCTGGGCCTT CACCCGAACT TGGGGGGTGG GGTGGGGAAA AGGAAGAAAC GCGGGGCGTAT 5110           5120           5130           5140           5150           5160
TGGCCCCAAT GGGGTCTCGG TGGGGTATCG ACAGAGTGCC AGCCCTGGGA CCGAACCCG
```

FIG. 7L

```
5170       5180       5190       5200       5210       5220
CGTTTATGAA CAAACGACCC AACACCGTGC GTTTTATTCT GTCTTTTTAT TGCCGTCATA 5230       5240       5250       5260       5270       5280
GCGCGGGTTC CTTCCGGTAT TGTCTCCTTC CGTGTTTCAG TTAGCCTCCC CCTAGGGTGG 5290       5300       5310       5320       5330       5340
GCGAAGAACT CCAGCATGAG ATCCCCGCGC TGGAGGATCA TCCAGCCGGC GTCCCGGAAA 5350       5360       5370       5380       5390       5400
ACGATTCCGA AGCCCAACCT TTCATAGAAG GCGGCGGTGG AATCGAAATC TCGTGATGGC 5410       5420       5430       5440       5450       5460
AGGTTGGGCG TCGCTTGGTC GGTCATTTCG AACCCCAGAG TCCCGCTCAG AAGAACTCGT 5470       5480       5490       5500       5510       5520
CAAGAAGGCG ATAGAAGGCG ATGCGCTGCG AATCGGGAGC GGCGATACCG TAAAGCACGA 5530       5540       5550       5560       5570       5580
GGAAGCGGTC AGCCCATTCG CCGCCAAGCT CTTCAGCAAT ATCACGGGTA GCCAACGCTA 5590       5600       5610       5620       5630       5640
TGTCCTGATA GCGGTCCGCC ACACCCAGCC GGCCACAGTC GATGAATCCA GAAAAGCGGC
```

FIG. 7M

```
5650       5660       5670       5680       5690       5700
CATTTTCCAC CATGATATTC GGCAAGCAGG CATCGCCATG GGTCACGACG AGATCCTCGC 5710       5720       5730       5740       5750       5760
CGTCGGGCAT GCTCGCCTTG AGCCTGGCGA ACAGTTCGGC TGGCGCGAGC CCCTGATGCT 5770       5780       5790       5800       5810       5820
CTTGATCATC CTGATCGACA AGACCGGGCTT CCATCCGAGT ACGTGCTCGC TCGATGCGAT 5830       5840       5850       5860       5870       5880
GTTTCGCTTG GTGGTCGAAT GGGCAGGTAG CCGGATCAAG CGTATGCAGC CGCCGCATTG 5890       5900       5910       5920       5930       5940
CATCAGCCAT GATGGATACT TTCTCGGCAG GAGCAAGGTG AGATGACAGG AGATCCTGCC 5950       5960       5970       5980       5990       6000
CCGGCACTTC GCCCAATAGC AGCCAGTCCC TTCCCGCTTC AGTGACAACG TCGAGCACAG 6010       6020       6030       6040       6050       6060
CTCGCAAGG AACGCCCGTC GTGGCCAGCC ACGATAGCCG CGCTGCCTCG TCTTGCAGTT 6070       6080       6090       6100       6110       6120
CATTCAGGGC ACCGGACAGG TCGGTCTTGA CAAAAGAAC CGGGGCGCCCC TGCGCTGACA
```

```
      6130       6140       6150       6160       6170       6180
GCCGGAACAC GGCGGGCATCA GAGCAGCCGA TTGTCTGTTG TGCCCAGTCA TAGCCGAATA 6190       6200       6210       6220       6230       6240
GCCTCTCCAC CCAAGCGGGCC GGAGAACCTG CGTGCAATCC ATCTTGTTCA ATCATGCGAA 6250       6260       6270       6280       6290       6300
ACGATCCTCA TCCTGTCTCT TGATCGATCT TTGCAAAAGC CTAGGCCTCC AAAAAAGCCT 6310       6320       6330       6340       6350       6360
CCTCACTACT TCTGGAATAG CTCAGAGGCC GAGGCGGGCCT CGGCCTCTGC ATAAATAAAA 6370       6380       6390       6400       6410       6420
AAAATTAGTC AGCCATGGGG CGGAGAATGG GCGGAACTGG GCGGAGTTAG GGGCGGGATG 6430       6440       6450       6460       6470       6480
GGCGGAGTTA GGGGCGGGAC TATGGTTGCT GACTAATTGA GATGCATGCT TTGCATACTT 6490       6500       6510       6520       6530       6540
GGGCCTGCTG GGGAGCCTGG GGACTTTCCA CACCTGGTTG CTGACTAATT GAGATGCATG 6550       6560       6570       6580       6590       6600
CTTTGCATAC TTCTGCCTGC TGGGGAGCCT GGGACTTTC CACACCCTAA CTGACACACA
```

```
   6610         6620         6630         6640         6650         6660
TTCCACAGCT   GGTTCTTTCC   GCCTCAGGAC   TCTTCCTTTT   TCAATAAATC   AATCTAAAGT 6670         6680         6690         6700         6710         6720
ATATATGAGT   AAACTTGGTC   TGACAGTTAC   CAATGCTTAA   TCAGTGAGGC   ACCTATCTCA 6730         6740         6750         6760         6770         6780
GCGATCTGTC   TATTTCGTTC   ATCCATAGTT   GCCTGACTCC   CCGTCGTGTA   GATAACTACG 6790         6800         6810         6820         6830         6840
ATACGGGAGG   GCTTACCATC   TGGCCCCAGT   GCTGCAATGA   TACCGCGAGA   CCCACGCTCA 6850         6860         6870         6880         6890         6900
CCGGCTCCAG   ATTTATCAGC   AATAAACCAG   CCAGCCGGAA   GGGCCGAGCG   CAGAAGTGGT 6910         6920         6930         6940         6950         6960
CCTGCAACTT   TATCCGCCTC   CATCCAGTCT   ATTAATTGTT   GCCGGGAAGC   TAGAGTAAGT 6970         6980         6990         7000         7010         7020
AGTTCGCCAG   TTAATAGTTT   GCGCAACGTT   GTTGCCATTG   CTACAGGCAT   CGTGGTGTCA
```

FIG. 7P

```
      7030       7040       7050       7060       7070       7080
CGCTCGTCGT TTGGTATGGC TTCATTCAGC TCCGGTTCCC AACGATCAAG GCGAGTTACA 7090       7100       7110       7120       7130       7140
TGATCCCCCA TGTTGTGCAA AAAAGCGGTT AGCTCCTTCG GTCCTCCGAT CGTTGTCAGA 7150       7160       7170       7180       7190       7200
AGTAAGTTGG CCGCAGTGTT ATCACTCATG GTTATGGCAG CACTGCATAA TTCTCTTACT 7210       7220       7230       7240       7250       7260
GTCATGCCAT CCGTAAGATG CTTTTCTGTG ACTGGTGAGT ACTCAACCAA GTCATTCTGA 7270       7280       7290       7300       7310       7320
GAATAGTGTA TGCGGCGACC GAGTTGCTCT TGCCCGGCGT CAATACGGGA TAATACCGCG 7330       7340       7350       7360       7370       7380
CCACATAGCA GAACTTTAAA AGTGCTCATC ATTGGAAAAC GTTCTTCGGG GCGAAAACTC 7390       7400       7410       7420       7430       7440
TCAAGGATCT TACCGCTGTT GAGATCCAGT TCGATGTAAC CCACTCGTGC ACCCAACTGA 7450       7460       7470       7480       7490       7500
TCTTCAGCAT CTTTTACTTT CACCAGCGTT TCTGGGTGAG CAAAAACAGG AAGGCAAAAT 7510       7520       7530       7540       7550       7560
```

```
GCCGCAAAAA AGGGAATAAG GGCGACACGG AAATGTTGAA TACTCATACT CTTCCTTTTT
     7570       7580       7590       7600       7610       7620
CAATATTATT GAAGCATTTA TCAGGGTTAT TGTCTCATGA GCGGATACAT ATTTGAATGT
     7630       7640       7650       7660       7670       7680
ATTTAGAAAA ATAAACAAAT AGGGGTTCCG CGCACATTTC CCCGAAAAGT GCCACCTGAC
     7690       7700       7710       7720       7730       7740
GCGCCCTGTA GCGGCGCATT AAGCGCGGCG GGTGTGGTGG TTACGCGCAG CGTGACCGCT
     7750       7760       7770       7780       7790       7800
ACACTTGCCA GCGCCCTAGC GCCCGCTCCT TTCGCTTTCT TCCCTTCCTT TCTCGCCACG
```

FIG. 7S

```
7810        7820        7830        7840        7850        7860
TTCGCCGGGCT TTCCCCGTCA AGCTCTAAAT CGGGGGCTCC CTTTAGGGTT CCGATTTAGT 7870        7880        7890        7900        7910        7920
GCTTTACGGGC ACCTCGACCC CAAAAAACTT GATTAGGGTG ATGGTTCACG TAGTGGGCCA 7930        7940        7950        7960        7970        7980
TCGCCCTGAT AGACGGTTTT TCGCCCTTTG ACGTTGGAGT CCAGTTCTT TAATAGTGGA 7990        8000        8010        8020        8030        8040
CTCTGTTCC AAACTGGAAC AACACTCAAC CCTATCTCGG TCTATTCTTT TGATTTATAA 8050        8060        8070        8080        8090        8100
GGGATTTTGC CGATTTCGGC CTATTGGTTA AAAAATGAGC TGATTTAACA AAAATTTAAC 8110        8120        8130        8140        8150        8160
GCGAATTTTA ACAAAATATT AACGCTTACA ATTTAC.....
```

SYSTEM FOR ISOLATING AND IDENTIFYING EUKARYOTIC CELLS TRANSFECTED WITH GENES AND VECTORS, HOST CELLS AND METHODS THEREOF

BACKGROUND OF THE INVENTION

This invention was made with Government support under Grant No. DK48845 with the National Institutes of Health (NIH). The Government may have certain rights in this invention.

FIELD OF THE INVENTION

The present invention relates generally to the fields of cell biology, molecular biology and immunology and, more specifically, to a novel system of identifying and isolating cells transfected with vectors encoding genes of interest. Use of this novel system allows rapid selection of transfected cells from total populations of cells in culture.

BACKGROUND INFORMATION

Introduction

Recent advances in molecular biology have allowed the production of recombinant immunoglobulin molecules (rAbs) from existing hybridomas, as described in Morrison, S. L., et al., *Clin. Chem.* 34:1668 (1988); Orlandi, R., et al., *Proc. Natl. Acad. Sci.* (1989); Larrick, J. W., et al., *Biochem. Biophys. Res. Commun.* 160:1250 (1989) and de novo from phage display libraries as described in McCafferty, J., et al., *Nature* 348:552 (1990); Clackson, T., et al., *Nature* 352:624 (1991); Marks, J. D., et al., *J. Mol. Biol.* 222:581 (1991); Hoogenboom, H. R., et al., *Nucl. Acids Res.* 19:4133 (1991); Winter, G. et al., *Annu. Rev. Immunol.* 12:433 (1994). Recombinant immunoglobulin molecules (rAbs), including single chain antibodies (sFvs) and Fabs, are able to bind their cognate antigens with high specificity and affinity, as described in Winter, G., et al., *Annu. Rev. Immunol.* 12:433 (1994). These modular binding regions can be fused with bioactive proteins or drugs and used to direct these molecules to their intended site of action, as described in Siegall, C. B., et al., *J. Immunol.* 152:2377 (1994). By using phage display technology, rAbs can now be isolated and produced in vitro against molecules, both natural and synthetic, that are either non-immunogenic or of such a high toxicity as to preclude their production in vivo, as described in McCafferty, J., et al., *Nature* 348:552 (1990); Clackson, T., et al., *Nature* 352:624 (1991); Hoogenboom, H. R., et al., *Nucl. Acid Res.* 19:4133 (1991); Marks et al., J. D., *J. Mol. Biol.* 222:581 (1991); Winter, G., et al., *Annu. Rev. Immunol.* (1994). The power and versatility of these proteins allows rAbs to be used in ways that conventional antibodies could not.

The present invention uses such recombinant antibody binding units, in conjunction with expression vectors coding for genes of interest, as "molecular hooks" to identify and separate transfected cells from a culture. The present invention allows for identification and selection of transfected cells as early as two hours after transfection, thus allowing study of the acute effects of the expression of the gene of interest.

The use of the invention's "molecular hooks" will assist in the identification and characterization of many cellular signaling factors heretofore not possible with current technology. Such identification and characterization has been possible only as a result of the development of technology enabling the introduction of expression plasmids into mammalian cells. The subsequent examination of the effect (on cellular growth and differentiation) of constitutively expressing an otherwise tightly regulated molecule has permitted the elucidation of many complex signaling pathways. With current technology, not all of the functional characteristics of signaling molecules are readily detectable using these systems. For example, it would be of great value to study the effect of dominant negative mutations of signaling molecules in both transformed and primary cells. Those negative or toxic mutations that result in inhibition of cell growth or cell death may be masked due to the low efficiency of transfection. In addition, it is not possible to increase the population of cells expressing a gene of interest by selecting for stable transformants as negative growth phenotypes are not amenable to this type of selection. This limitation of current technology in expression systems has, to a limited extent, been addressed by the use of inducible promoter systems, see, for example, those described in Levinson, A. D., "Gene Expression Technology," In D. V. Goeddel (Ed.), *Methods in Enzymology*, Academic Press, p. 497 (1991). However, this approach is not always optimal or applicable and has met with varied success depending on the cell type and origin of the promoter utilized. If cells expressing dominant-negative signaling molecules could be selected from culture soon after, within hours, of transfection, rather than days or weeks later, as is the case with current technology, assessment of the effects of the expression of a potentially negative effector would be possible. Similarly, early enrichment of transfected cells would allow studies of acute expression of transfected genes in homogeneously expressing cell cultures.

Selection of primary cell cultures that do not divide, such as neuronal cell cultures, have been limited to techniques that involve negative selection, such as antibiotic resistance conferred by the transfected vector. Selection of transfected cells by utilizing resistance to antibiotics takes days. In contrast, selection of primary cultures with the vectors of the instant invention allows selection as soon as 2 hours after the transfection event, depending on the primary cell culture.

The present invention is a novel alternative technology, encompassing a new expression system that will enable selection of transfected cells from culture to be carried out soon after, within 2 hours, of the transfection event, along with other advantages that will become apparent below.

The present invention satisfies these needs and provides related advantages as well.

SUMMARY OF THE INVENTION

The present invention relates to a eukaryotic expression vector for the identification and separation of transfected cells from a total cell population, comprising: a first DNA sequence encoding an anti-hapten recombinant antibody, said recombinant antibody capable of binding a specific hapten; a second DNA sequence encoding for a transmembrane domain functionally linked to said first DNA sequence; a third DNA sequence encoding for a signal sequence functionally linked to said first DNA sequence; a first promoter operatively linked to said first DNA sequence; a fourth DNA sequence encoding for at least one protein; a promoter operatively linked to said fourth DNA sequence.

The invention also relates to a mixture of eukaryotic expression vectors for the identification and separation of transfected cells from a total cell population comprising a first vector which in turn comprises: a first DNA sequence encoding an anti-hapten recombinant antibody, said recombinant antibody capable of binding a specific hapten; a second DNA sequence encoding for a transmembrane domain functionally linked to said first coding sequence; a third DNA sequence encoding for a signal sequence functionally linked to said first DNA sequence; and a promoter operatively linked to said first DNA sequence.

The invention also relates to a method of identifying and isolating transfected cells from the total cell population, comprising: transfecting a eukaryotic cell with a eukaryotic expression vector; exposing said cell to a hapten conjugated to a cell selection means; separating said cell, bound to said selection means, from the total cell population.

The invention also relates to a kit for the identification and separation of transfected cells from a total cell population, comprising a eukaryotic expression vector and a cell separation means.

The invention also relates to cells transfected with the expression vectors of the invention.

BRIEF DESCRIPTION OF THE DRAWINGS

FIGS. 1A–1,1A–2 and 1B demonstrate features and the plasmid map of the eukaryotic expression vector pPhOx.TM, which encodes for an anti-hapten (anti-phOx) sFv.

FIG. 2 demonstrates the in vitro transcription and translation product of pPhOx.TM using an SDS polyacrylamide gel autoradiogram. As seen in lane 3, the transcription/translation reaction produced a protein of the expected molecular weight, which is approximately 30 kD (phOx sFv) plus 7.6 kD (the PDGFR transmembrane domain), totaling approximately 40 kD. Note lane 1 contains the positive control beta-galactosidase encoding DNA and lane 2 contained no exogenous DNA.

The results demonstrate that most if not all of the cells expressing the functional pPhOx.TM product (cells with silver grains, denoted by arrows) are also expressing β-galactosidase (blue staining, the point of the triangles opposite the stars points towards representative cells staining for β-galactosidase). Greater than 98% of the cells selected with pPhOx-BSA-coated magnetic beads also stained positively for protein product of the experimental gene of interest, in this experiment, the β-galactosidase gene.

FIGS. 6A–6N set forth the DNA sequence (SEQ ID NOS: 1 and 2) of pPhOx.TM.

Figure 7A:
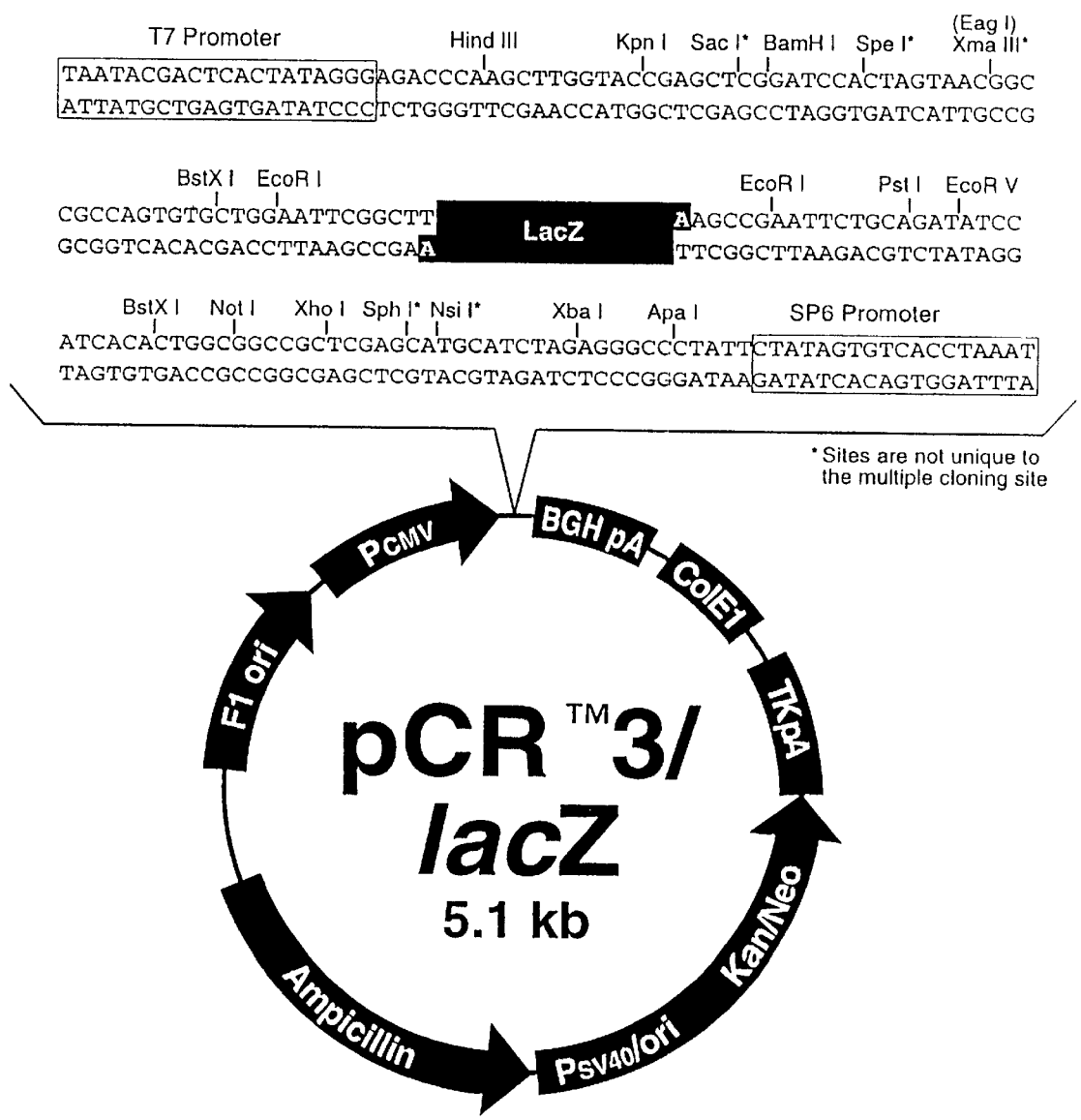

FIGS. 7A–7N set forth the DNA sequence (SEQ ID NOS: 3) of pCR™3lacZ.

DETAILED DESCRIPTION OF THE INVENTION

In the following description, reference will be made to various methodologies known to those skilled in the art of molecular genetics, immunology and general biology. Publications and other materials, as cited herein, setting forth such known methodologies to which reference is made, are incorporated herein by reference in their entireties as though set forth in full.

General principles of antibody engineering are set forth in *Antibody Engineering*, 2nd edition, Ed. C. A. K. Borrebaeck, Oxford Univ. Press (1995). General principles of protein engineering are set forth in *Protein Engineering*, A Practical Approach, Ed. Rickwood, D., et al., IRL Press at Oxford Univ. Press, Oxford, Eng. (1995). General principles of antibodies and antibody binding to haptens are set forth in: Nisonoff, A., *Molecular Immunology*, 2nd edition, Sinauer Associates, Sunderland, Mass. (1984); and, Steward, M. W., *Antibodies, Their Structure and Function*, Chapman and Hall, New York, N.Y. (1984).

The present invention generally relates to a novel system of identifying and separating cells transfected with a gene of interest. Such a system allows the study of experimental genes of interest on cellular events soon after transfection, as described above in the Summary. In a preferred embodiment, cells transfected with the expression system of the invention can be selected and experimented on as soon as 2 hours post-transfection.

This new technology, the present invention, thereby aids in the identification and characterization of genes of experimental interest soon after transfection. Intracellular signaling proteins and dominant-negative signaling molecules are now accessible to study. Early events initiated by dominantly acting oncogenes, negatively acting tumor suppressors, as well as temporal events along differentiated pathways can now be studied.

For example, signaling pathways in cell lines derived from a certain tumor type can be studied with the present invention. The invention can be used to study the role of the HER-2/neu oncogene in breast carcinoma by expressing dominant negative mutations of signaling proteins in breast cancer cell lines. HER-2/neu (c-erbB-2) is overexpressed in 30% of breast tumors and its presence is correlated with lower survival rates of patients with these tumors (Elledge, R. M., et al., *Seminars in Oncology* 19:244 (1992). The HER-2/neu protein demonstrates close sequence homology with, but is distinct from, the epidermal growth factor receptor (EGFR) (Scheuter, A. L., et al., *Science* 229:976 (1985). The unregulated growth characteristics of HER-2/neu-positive tumors is hypothesized to arise, at least in part, from the effect of HER-2/neu on intracellular signaling pathways (Kumar, R., et al., *Mol. Cell. Biol.* 11:979 (1991)). The invention described herein can be used to isolate homogeneous populations of cells expressing dominant negative mutations of cellular signaling proteins known to interact with the EGF receptor such as PI3K, PLCγ1, Grb2, Syp, Nck, Shc, and p91 in several cell lines derived from breast tumors (see Table I).

TABLE 1

Properties of cell lines derived from carcinoma of the breast

| Cell Type | EGFR | HER2/neu | Tumor-igenic in Nude Mice | Derived From |
|---|---|---|---|---|
| MDA-MB-468 | + | -- | + | Human adenocarcinoma of breast, from pleural effusion |
| MDA-MB-453 | -- | + | -- | Human carcinoma of breast from effusion |
| MCF-7 | -- | -- | + | Human adenocarcinoma of breast, from pleural effusion |
| SKBR-3 | + | + | + | Human adenocarcinoma of breast, from malignant pleural effusion |

For another example, efficient study of regulatory proteins, such as early events in the Ras-regulated serine/threonine kinase pathways, requires a transfection system that allows rapid selection of transfected cells. The present invention will allow an analysis of when this pathway diverges into the Ras-MEK-MAPK axis and the Ras-MEKK-SEK-SAPK (JNK) axis (Sanchez, I., et al., *Nature* 372:794 (1994); Yan, M., et al., *Nature* 372:798 (1994); Derijard, B., et al., *Science* 267:682 (1995)).

This expression system of the invention, by giving researchers the ability to select cells expressing genes of interest from culture as soon as 2 hours after transfection, allows the study of the acute effects of expression of a wide variety of experimental systems otherwise not accessible to study. For example, dominant negative or constitutively active mutations of proteins involved in signal transduction can be studied using the present invention. Analyses of early transcription events are now accessible to study. Experimentation on the acute effects of transfection on primary cell cultures, including cells that normally do not divide, such as neurons, is now possible.

The present invention relates to a novel system for rapidly isolating and identifying eukaryotic cells after transfection. The invention employs a vector encoding for a "molecular hook," including an rAb or a receptor-like molecule, that is expressed on the cell's surface. Such expression may occur as early as 2 hours after transfection. The rAb binds to a specific "hapten," which, as defined below, can be any unique, selective epitope. Structurally, the rAb can be in the form of double or single chain antibody (sFv), an Fab fragment, or any functional binding unit.

The invention's use of the rAb binding domain on the transfected cell and the hapten on the cell selection means has advantages over the converse option (the hapten expressed on the transfected cell). First, it is advantageous to have a high density of hapten or epitope on the cell selection means, such as a bead. Second, it is advantageous to have the entity that has a higher level specific binding, i.e. less cross-reactivity with irrelevant molecules, on the cell selection means. The rAb or receptor-like molecule has a greater possibility of cross-reactivity than the hapten or epitope molecule. The cell selection means, with a high hapten density and binding specificity, will yield a relatively pure population of cells transfected with and expressing the requisite rAb or receptor-like molecule.

In another embodiment of the invention, in place of the rAb, the "selective hook" expressed on the cell's surface is a receptor-like or adhesion molecule capable of selectively binding to a specific hapten, epitope or ligand. One skilled in the art would have the means to select receptor-like or adhesion molecule binding domains for purposes of incorporation into the eukaryotic expression vector of the invention. As used herein, the term "receptor-like" molecule means any protein capable of specifically binding a hapten, epitope, or ligand. Examples of protein binding sites, to be expressed on the cell's surface, that can be used to selectively bind epitopes or haptens, include adhesion molecules such as cadherins, selecting, fasciclins, integrins, leukocyte adhesion receptor, neuroglian, VLA family molecules and the like. Examples of protein binding sites that can be used to selectively bind include growth factor receptor binding sites, including growth hormone receptor, insulin receptor, interleukin receptors and the like. Examples of specific protein binding interactions useful in the instant invention are described in Creighton, T. E., in *Proteins, Structure and Molecular Principles*, W. H. Freeman and Company, New York, N.Y. (1984); and, adhesion molecules are described in Pigott, R., et al., in *The Adhesion Molecule*, Academic Press, Harcourt Brace & Co., New York, N.Y. (1993). These references, as all references cited herein, are incorporated by reference in their entirety.

The rAb and receptor-like or adhesion molecule are also engineered to include coding sequences for a transmembrane domain or any membrane anchoring sequence and a secretion signal (leader sequence), thus allowing its expression on the transfected cell's outer membrane surface (i.e., extracellular expression). All coding sequences include 3' eukaryotic polyadenylation (poly-A) sequences, for the necessary 3' poly-adenylic acid RNA sequence needed.

Once expressed on the cell's outer membrane surface, the rAb or receptor-like domain is capable of binding to a specific hapten or epitope. This hapten or epitope is bound either directly or indirectly to a cell separation means, such as magnetic beads or sheets, tubes, porous matrices, or any natural or synthetic material including metals, polymers, latex beads, agarose, Sepharose, or any solid surface. The hapten or epitope can also include or be conjugated to a fluorescent or other labeled, selectable hapten or epitope. An example is PhOx-BSA-FITC. This allows for identification and selection of the transfected cell shortly after transfection, which can be as soon as approximately 2 hours after transfection, depending on the experimental system.

The transfected cells can be separated from unbound, untransfected cells by any physical means, such as filtration, isolation, by magnetic field, centrifugation, washing and the like. This rapid enrichment of transfected cells allows studies of the acute expression of the transfected experimental genes of interest.

The eukaryotic expression vector of the invention can use any vector or mixture of vectors capable of transfection and expression of DNA in eukaryotic cells. Such vectors are well known in the art and include, but are not limited to plasmids, viruses (such as adenoviruses, bovine papillomavirus, Epstein Barr virus, papovavirus, and retroviruses) or linear, double-stranded DNA. For example, retrovirus vectors are described in Somia, N. V., et al., *Proc. Natl. Acad. Sci.* 92:7570 (1995). Additional vectors are described in *Catalogue of Recombinant DNA Materials,* 2nd Edition, ATCC, Parklawn, Md. (1991); and viral vectors are described in Levinson, A. D., "Expression of Heterologous Genes in Mammalian Cells", In *Methods in Enzymology* 185:485 (1990). One skilled in the art would know how to choose a vector of choice for a particular eukaryotic cell line or experimental system. Vectors are available to one skilled in the art that, upon transfection, are transient and episomal, stable and episomal, or stable and integrated. The vector containing the experimental gene(s) of interest can be encoded within the same vector as the rAb or can be on another or mixture of other vectors. If a mixture of vectors are used, they are co-transfected.

The rAb is designed to bind to a specific hapten or epitope. As used herein, the term "hapten" or "epitope" means any organic or inorganic molecule capable of being bound by any rAb or recombinant receptor-like molecule, and includes molecule that can serve as a ligand for receptor-like or adhesion molecules. As noted above, by using phage display technology, rAbs can now be isolated and produced in vitro against "hapten" molecules, both natural and synthetic, that are either non-immunogenic or of such a high toxicity as to preclude their production in vivo. If small rigid haptens are used, antibody/hapten affinities as high as $10^{12}$ M-1 can be generated, as described in Searle, S. J., et al., Antibody Structure and Function, In Antibody Engineering, 2nd Ed, Ed. C. A. K. Borrebaeck, Oxford Univ. Press (1995). Thus, for the purpose of this invention, a hapten is defined as not only any molecule that is immunogenic either alone or conjugated to a carrier but any molecule capable of binding to an rAb as described above. Such hapten molecules include aniline derivatives such as: diazonium salts; benzene and derivatives such as dinitro-benzenesulfonate or dinitrobenzene or p-amino-benzenearsonate; phenol and derivatives as dinitrophenol (DNP), DNP-lysine; benzoates and benzoate derivatives such as phenylazobenzoate; acetates and derivatives such as phenylacetate; and the like. Analysis of haptens and Ab-hapten interactions are described in Nisonoff, A., *Molecular Immunology,* 2nd edition, Sinauer Associates, Sunderland, Mass. (1984); and, Steward, M. W., *Antibodies, Their Structure and Function,* Chapman and Hall, New York, N.Y. (1984).

As used herein, the term "antibody binding unit" means any functional protein unit which can bind a hapten. Therefore, structurally, the recombinant rAb protein can be designed to take the final form of a double or single chain antibody (designated "sFv"), Fab, Fab' or F(ab')$_2$ fragments, or any functional antigen-antibody binding unit. rAbs, including single chain antibodies (sFvs) and Fabs, are able to bind their cognate antigens with high specificity and affinity, as described in Winter, G., et al., *Annu. Rev. Immunol.* 12:433 (1994). By using phage display technology, rAbs can now be isolated and produced in vitro against molecules, both natural and synthetic, that are either non-immunogenic or of such a high toxicity as to preclude their production in vivo, as described in: Clackson, T., et al., *Nature* 352:624 (1991); Figini, M., et al., *J. Mol. Biol.* 239:68 (1994); Hawkins, R. E., et al., *J. Mol Biol.* 226:889 (1992); Hoogenboom, H. R., et al., *Immunol. Rev.* 130:41 (1992); Hoogenboom, H. R., et al., *Nucl. Acid Res.* 19:4133 (1991); Jespers, L. S., et al., *Biotechnology* 12:899 (1994); Marks et al., J. D., *J. Mol. Biol.* 222:581 (1991); McCafferty, J., et al., *Nature* 348:552 (1990); Winter, G., et al., *Annu. Rev. Immunol.* 12:433 (1994). The synthesis of single-stranded sFv antibody fragment gene repetoires is also described by Marks, J. D., "Human Monoclonal Antibodies from V-Gene Repertoires Expressed on Bacteriophage," In *Antibody Engineering,* 2nd Ed, Ed. C. A. K. Borrebaeck, Oxford Univ. Press (1995). Hilyard, K. L. discusses "Protein Engineering of Antibody Combining Sites" In *Protein Engineering,* edited by Rees, A. R. et al., IRL Press at Oxford Univ. Press, New York, N.Y. (1992). As noted above, all references cited herein are incorporated by reference in their entirety.

In the rAb-containing vectors of the invention, the coding sequence for the rAb is operably linked to a strong constitutive promoter capable of expression immediately upon transfection or soon thereafter. As disclosed herein, this enables selection of cells expressing genes of interest, through the extracellular expression of the rAb, within hours after transfection. Such constitutive promoters are well known in the art and include, but are not limited to viral, bacterial or eukaryotic promoters. One skilled in the art would know how to choose a vector of choice for a particular experimental system. Examples of strong constitutive promoters include cytomegalovirus (CMV) immediate early promoter, Rous sarcoma virus (RSV) promoter, adenovirus major late promoter, the lac-inducible promoter, SV40 early promoter and retroviral long terminal repeats (LTRs).

Alternatively, the rAb can be operatively linked to an inducible promoter, such as interferon beta promoter, heat-shock promoter, glucocorticoid promoter and the like, as generally described in Lewin, B., *Genes V,* Oxford Univ. Press, New York, N.Y. (1994). In this situation, the rAb is expressed on the cell surface and the transfected cell can be identified and isolated from the total cell population as soon as two hours after induction of the promoter.

One skilled in the art would know how to choose additional genetic elements necessary for an experimental system, such as the need to include enhancers within an expression vector, as discussed by Kriegler, M., "Assembly of Enhancers, Promoters, and Splice Signals to Control Expression of Transferred Genes," In *Methods in Enzymology* 185:512 (1990).

One or more genes of interest to be expressed in the transfected cell of the instant invention can be contained within a second vector. The second vector can be co-transfected with the rAb encoding vector. Alternatively, it can be spliced within the rAb-encoding vector.

The experimental gene(s) can be operatively linked to the same or a similar type of strong constitutive promoter as the rAb. Alternatively, it can be operatively linked to a different promoter. This promoter can be an inducible promoter, such as interferon beta promoter, heat-shock promoter, glucocorticoid promoter and the like, as described in Lewin, B., *Genes V*, Oxford Univ. Press, New York, N.Y. (1994). If the gene of interest or the rAb is operatively linked to an inducible promoter, that rAb or gene can be expressed on the cell's surface as soon as two hours after induction. Alternatively, the experimental gene(s) of interest can be operatively linked to the same promoter as the rAb. This can be effected by inserting an Internal Ribosome Entry Site (IRES) between the coding region for the rAb and the second, downstream, gene (Glass, M. J., et al., *Virology* 193(2):842–852 (1993)).

In designing and synthesizing the promoters, they can be initially placed within the expression vector or genome or can be synthesized in conjunction with the rAb or gene of interest before splicing into their respective vector(s). A polylinker can be designed between the promoter and a poly A sequence for simplified insertion of rAb or gene of interest coding sequences in the expression vector or genome.

In one embodiment of the present invention, the vector of the expression vector is pCR3.1 (Invitrogen, San Diego, Calif). pCR3.1 is a eukaryotic expression vector which includes polylinker sites, cytomegalovirus (CMV) promoter, bovine growth hormone (bGH) poly A signal and the ampicillin and neomycin resistance genes for selection, as described in FIGS. 1A–1, 1A–2 and 1B.

The rAb sequence is linked to a signal, or leader, sequence that is functional in the transfected host cell. Such signal sequences, also called leader sequences, are well known in the art. A signal sequence is composed of 15–30 amino acids that are relatively hydrophobic, thus allowing insertion into microsomal membrane. One skilled in the art would know how to choose an appropriate signal (leader) sequence for a particular eukaryotic cell line or experimental system. For example, the leader sequence can be either homologous or heterologous to the transfected host. The desired rAb coding sequence can be linked to any signal (leader) sequence which will allow insertion of the rAb protein in the membrane of the selected host and its expression as a functional, hapten-binding extracellular protein. In one embodiment of the invention, the rAb sFv coding sequence was combined with the murine kappa chain V-J2-C region signal peptide. This signal peptide is described in Coloma, M. J., et al., *J. Immunol. Methods* 152:89 (1992) and Kabat, E. A., et al., *Sequences of Proteins of Immunological Interest*, 4th ed. U.S. Dept. of Health and Human Services. Washington, D.C. (1987).

The rAb and receptor-like coding sequences are also linked to a transmembrane domain, or any membrane anchoring sequence. One skilled in the art would know how to choose an appropriate transmembrane domain sequence for a particular eukaryotic cell line or experimental system. The desired rAb coding sequence can be linked to any transmembrane domain which will allow insertion of the rAb protein in the membrane of the selected host and its expression as a functional, hapten-binding extracellular protein. In one embodiment of the present invention, the rAb coding sequence is combined with the transmembrane domain of the human platelet derived growth factor receptor (PDGFR). The PDGFR transmembrane domain is described in Gronwald, G. M., et al., *Proc. Natl. Acad. Sci. U.S.A.* 85:3435 (1988).

In one embodiment of the present invention, the expression vector employs a single chain antibody (sFv) directed against a hapten, 4-ethoxymethylene-2-phenyl-2-oxazolin-5-one (phOx), to isolate transiently transfected cells from total populations in culture. The fusion protein, phOx sFv, as described in Hoogenboom, H. R., et al., *Nucl. Acids Res.* 19:4133 (1991), also contained two epitope tag peptides (for protein identification by anti-tag antibodies), and the transmembrane domain of the human PDGFR. When expressed in transfected cells, this fusion protein is anchored to the membrane via the transmembrane domain of the PDGFR. The functional antibody binding unit, phOx sFv, is therefore exposed to the extracellular environment. Cells were transiently transfected with an expression vector encoding phOx sFv, designated pPhox.TM. The cells were then selected from culture using antigen (phox)-coated magnetic beads (the method for cell separation by magnetic bead is described in detail, see Example III(b) below). Furthermore, when cells were co-transfected with pPhOx.TM and a plasmid containing the gene for β-galactosidase (pCMVβ, Clontech), greater than 98% of the cells selected from culture using the instant method were found to express β-galactosidase activity.

In this embodiment, use of a single-chained rAb, versus a dimeric rAb, is advantageous because the smaller size of the single chain coding sequence allows other inserted coding sequences to be longer without losing cloning efficiency. Cloning efficiency is inversely α to vector size. For example, if the gene of interest is cloned into the same vector as the rAb, then use of the smaller single-chained rAb allows for the inclusion (insertion) of a longer genes or multiple genes, of interest without increasing the overall size of the vector.

The cell selection means of the instant invention comprises any molecule or device that can be coupled to the hapten of choice and can be used to physically separate transfected cells from culture. For example, the hapten may be coupled directly or indirectly to any insoluble separation agent, including but not limited to magnetic beads, gelatin, glass, SEPHAROSE macrobeads or dextran microcarriers such as CYTODES® (Pharmacia, Uppsala, Sweden). The hapten may be coupled, either directly or indirectly, to plates, tubes, bottles, flasks, magnetic beads or sheets, tubes, porous matrices, or any natural or synthetic material including metals, polymers, latex beads, agarose, SEPHAROSE, or any solid surface and the like. Any molecule or reagent may be used to link to hapten of choice to the cell separation means, including lectins, avidin/biotin, inorganic or organic linking molecules and the like. The cell separation means may utilize antibodies specific for any chemical or biological reagent and any form of detection system known in the art. For example, methods of manufacturing antibodies and utilizing antibodies in detection and separation systems are described in *Antibodies, A Laboratory Manual*, edited by E. Harlow et al., Cold Spring Harbor Labs, Cold Spring Harbor, N.Y. (1989), which incorporated by reference in its entirety. The transfected cells can be separated from unbound, untransfected cells by any physical means, such as filtration, isolation, by magnetic field, centrifugation, washing and the like.

The transfection of any expression system can be effected by any means, physical or biological. Physical means include direct injection, or, DEAE-dextran mediated transfection, electroporation, calcium phosphate mediated or lipid-mediated transfection and the like.

The invention also relates to cells transfected with the expression vector and methods for selection and isolation of cells transfected with the expression system.

The following examples are intended to illustrate, but not limit, the present invention.

EXAMPLE I

Cloning Strategy for the Generation of Vector Capable of Expressing Single Chain Antibody Directed Against Hapten This example describes methods for the generation of a vector capable of expressing a single chain antibody directed against a hapten.

a. Construction of pPhOx.TM

Figure 1B:
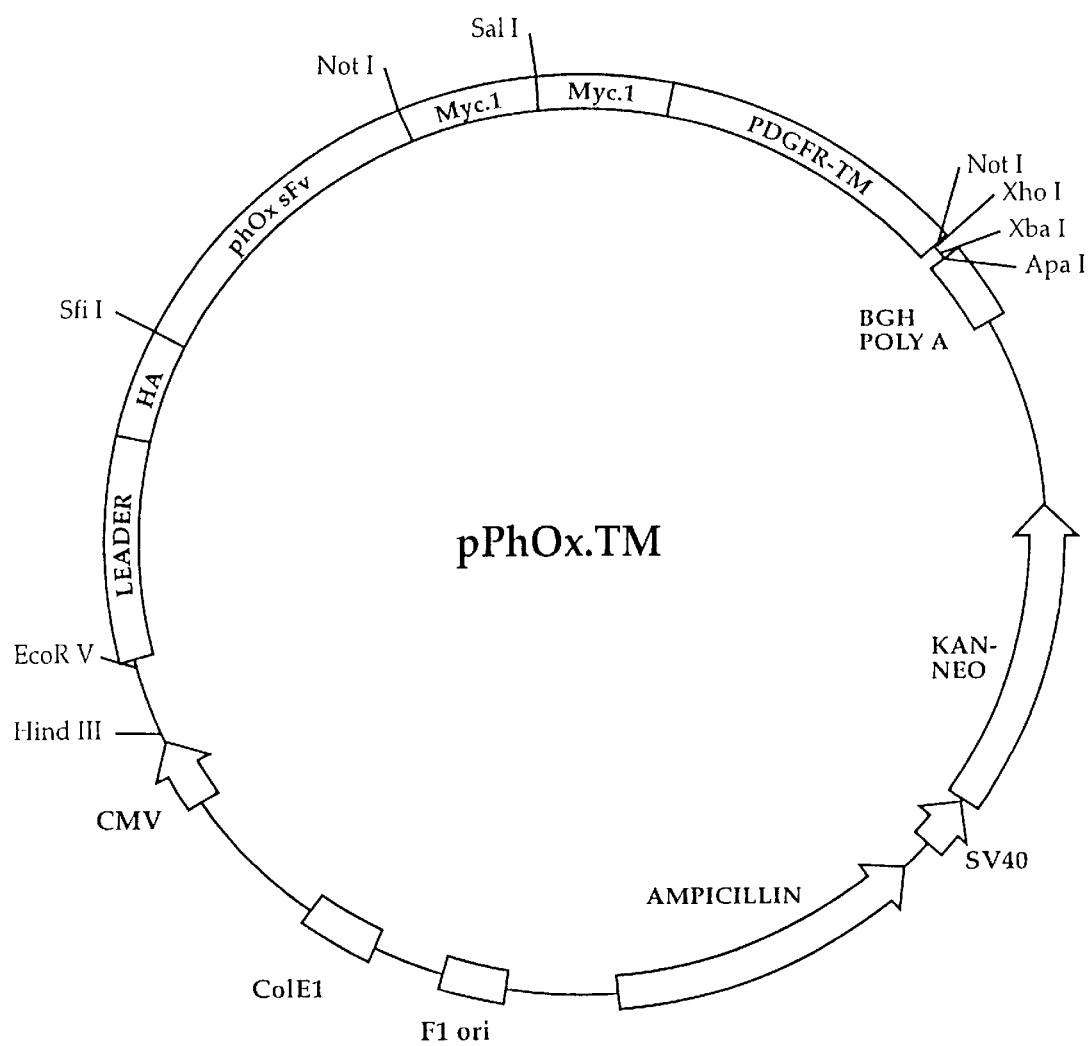
Figure 2:
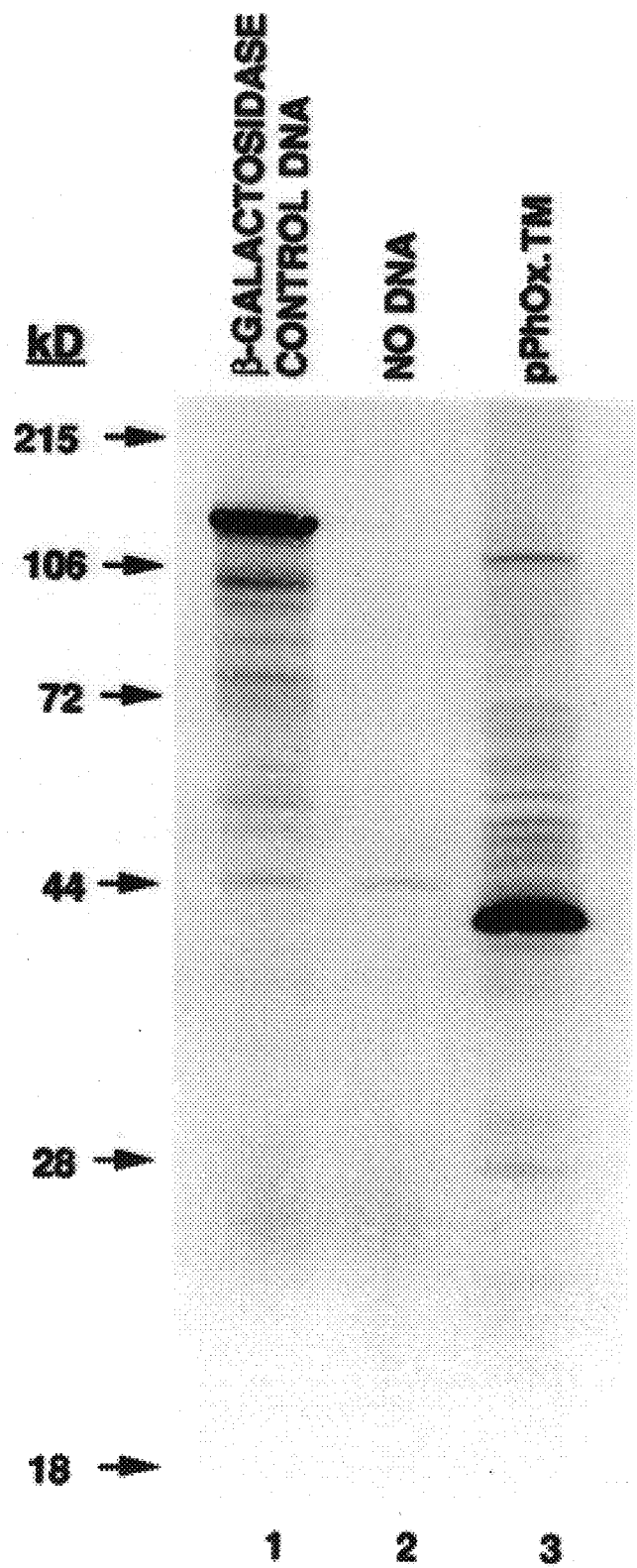

The parent vector for pPhOx.TM is pCR3.1 (Invitrogen, San Diego, Calif.), a eukaryotic expression vector containing the cytomegalovirus (CMV) promoter, bovine growth hormone (bGH), poly A signal and the ampicillin and neomycin resistance genes for selection, as described in FIGS. 1A–1 and 1A–2.

A DNA fragment encompassing the nucleotides encoding amino acids 514–562 of the human platelet-derived growth factor receptor (PDGFR) was amplified using nucleotide primers. PDGFR is described in Gronwald et al., *Proc. Natl. Acad. Sci. U.S.A.* 85:3435 (1988). These primers incorporate restriction sites and the Myc.1 epitope tag EQKLISEEDLN (SEQ ID NO.: 4), recognized by the monoclonal antibody 9E10.2, as described in Evan, G. I., et al., *Mol. Cell Biol.* 5:3610 (1985). This fragment was cloned into the T/A cloning vector PCRII (Invitrogen, San Diego, Calif.) and sequenced entirely on both strands to verify integrity. The PDGFR transmembrane fragment was constructed to contain a unique Sal I restriction site at the 5' end that is in the same reading frame as a Sal I site introduced at the 3' end of the phOx sFv sequence. This fragment was also constructed to contain a Not I site at its 3' end immediately following a stop codon which follows amino acid 562 of the human PDGFR sequence. The PDGFR DNA fragment was excised from the pCRII vector by digestion with Sal I and Not I, purified by standard procedures, and ligated into Sal I/Not I digested pCR3.1 vector thereby creating the vector pCR3.1.1.

The sequence encoding the murine Ig kappa-chain V-J2-C-region signal peptide (METDTLLLWVLLLWVPGSTGD) (SEQ ID NO: 5) containing an EcorV site at its 5' end, an influenza hemagglutinin (HA) epitope tag (YPYDVPDYA) (SEQ ID NO: 6), and Sfi I and Sal I sites at its 3' end was then subcloned from another sFv-containing vector (pCR3.2) as an EcoRV to Sal I fragment (sFv is a single-stranded antibody specific for 4-ethoxymethylene-2-phenyl-2-oxazolin-5-one, also designated phOx). This fragment was then ligated with EcoRV/Sal I digested pCR3.1.1 creating the vector pCR3.1.2.

The anti-phOx sFv was amplified from the phage display vector pHEN-I (phOx) (Hoogenboom et al., 1991) using primers that encompassed the Sfi I site on the 5' end of the sFv and incorporated a Sal I site on the 3'end of the 3' Myc.1 tag already present in pHEN-I. The PCR product was cloned into pCRII and its sequence integrity determined by dideoxy sequencing. The resulting clone was then digested with Sfi I and Sal I, purified by standard procedures, and ligated with Sfi I/Sal I digested pCR3.1.2 creating pPhOx.TM, as illustrated in FIGS. 1A–1,1A–2 and 1B. As a result of the cloning strategy, the Myc.1 epitope tag was fused to the carboxyl-terminal end of the anti-phOx sFv as a tandem repeat. The HA epitope tag (recognized by the monoclonal antibody 12CA5, Boehringer Mannheim, Indianapolis, Ind.) was fused to the amino terminus immediately after the leader peptide cleavage site such that it is the first sequence in the mature protein. The two epitope tag peptides, one 3' and one 5' to the sFv, were included as controls for complete expression and membrane display of the fusion protein. Expression of the sFv/PDGFR fusion protein from this plasmid is driven by the cytomegalovirus (CMV) promoter, the sequence of which is included in FIGS. 6A–6N.

b. In Vitro Transcription/translation of pPhOx.TM

As an assay for the integrity of the sFv:PDGFR sequence, the fusion protein was expressed from pPhOx.TM in vitro using a rabbit reticulocyte lysate system (Novagen, Inc., Madison, Wisc.), as illustrated in FIG. 2. Production of an RNA transcript in this system relied on the T7 promoter that is found between the CMV promoter and the sFv sequence in pPhOx.TM. The protein translated from the resulting message is approximately 40 kD. The expected molecular weight of the phOx sFv:PDGFRTM fusion protein is approximately 37.6 kD (30 kD (phox sFv)+7.6 kD (PDGFR TM domain, amino acids 514–562)).

EXAMPLE II

Synthesis of a Hapten Capturing Agent

This example describes methods for the synthesis of a hapten capturing agent through its coupling to a cell separation means.

a. Coupling of the Hapten phOx to BSA 4-ethoxymethylene-2-phenyl-2-oxazolin-5-one (phox) (Sigma, St. Louis, Mo.) was coupled to bovine serum albumin (BSA) as described previously by Makela et al., *J. Exp. Med.* 148:1644 (1978). By analysis of the UV absorbance spectra of the product and comparison with the molar extinction coefficient ($\epsilon$) of PhOx (where concentration=absorbance at 352 nm/$\epsilon$), it was determined that under these conditions a coupling efficiency of 20 moles of phOx per mole of BSA was achieved.

b. Coupling of phOx-BSA a Cell Separation Means, Tosyl-activated Magnetic Beads

The phOx-BSA conjugate described above was coupled to tosyl-activated magnetic beads (DYNABEADS M-450, Dynal, Inc.) using the manufacturer's recommended protocol. Beads were suspended in 50 mM $NaHCO_3$, pH 9.5 to a concentration of $2\times10^8$ beads/ml. PhOx-BSA was added to a final concentration of 150 $\mu$g/ml and the bead/protein mixture was incubated at 4° C. for 24 hours with gentle rotation. The beads were washed extensively and stored at 4° C. in PBS/0.1% BSA/0.01% $NaN_3$ at a concentration of $2\times10^8$ beads/ml.

2) Alternatively, magnetic beads activated by carboxy groups can be attached to the BSA-phOx conjugate. Thus, 2 ml of 0.01 M sodium acetate buffer (pH 5.0); the phOx-BSA conjugate from above (2 mg), 2 ml of 0.45 micron carboxylpolystyrene-plated magneted beads and 1-ethyl-3-(dimethylaminoprophy) carbodiimide (EDAC, Sigma, St. Louis, Mo.) were combined in a 15 ml glass centrifuge tube. The suspension was vortexed and incubated for two hours at ambient temperature on a rotary mixer. The suspension was subjected to a strong magnetic field and the supernatent was decanted. The beads were resuspended in 4 ml of the sodium acetate buffer and repelleted with the magnetic field twice to wash away contaminants.

EXAMPLE III

Transfection and Selection of Cells

This example describes methods for transfection of cells and selection with hapten capturing agent through its coupling to a cell separation means.

a. Eukaryotic Cell Transfection

Following confirmation of the integrity of the phOx sFv:PDGFRTM coding sequences, as described in Example II above, transient expression was carried out in cultured cells.

Cell lines tested include the "293" adenovirus-transformed human kidney cells, the human adenocarcinomas of the breast described in Table I, and HeLa cells, as described in above. Cell lines were grown to approximately 50–70% confluence in either RPMI-1640 or Dulbecco's Modified Eagle's Medium (DMEM, GIBCO, Grand Island, N.Y.) supplemented with 10% fetal calf serum (FCS, Gemini Bioproducts, Inc., Calabasas, Calif.) and the media changed 24 hours prior to electroporation. Cells were harvested by incubation with trypsin or 3 mM EDTA/PBS for 5 minutes at 37° C. and collected by centrifugation (800–1000 g for 5 to 10 minutes at room temperature). The supernatant was decanted. The cell pellet was then resuspended to a concentration of $1 \times 10^7$ cells per ml in complete medium per 60 mm plate. The cells were pipetted up and down to break up cell clumps and achieve single cell suspension.

The cells, as described above, were transfected by combining 5 μg plasmid DNA with 0.2 ml cell suspension ($2 \times 10^6$ cells) and pulsing the mixture at 500 μF and 250 V in an IBI Gene Zapper. The electroporated cells were added to 5 ml media and incubated at 37° C. in a humidified $CO_2$ incubator. Adherent cells were harvested by incubation with PBS/3 mM EDTA and combined with cells that remained suspended. Cells were collected by centrifugation and resuspended in 0.5 ml medium to which $1.5 \times 10^5$ phOx-BSA coated magnetic beads would be added.

b. Cell Separation by Magnetic Bead

Transfected cells were collected by centrifugation and resuspended in 0.5 ml PBS/3 mM EDTA medium, to which $1.5 \times 10^5$ phOx-BSA coated magnetic beads will be added.

The magnetic beads were washed before use to remove the sodium azide. One microcentrifuge tube for each 60 mm plate of cells was set up. The magnetic bead slurry was vortexed to resuspend beads. 10 ul ($1.5 \times 10^6$ beads) was added into each microcentrifuge tube. The beads were washed by adding 1 ml complete medium to each tube and mixed by inversion 3 times. The beads were pelleted with a strong magnet or magnetic stand and pipet or aspirate off medium.

The cell/bead mixture was rotated for 30 minutes at 37° C. on a Dynal mixer. The bound cells were separated from the mixture by placing the tubes in a Dynal MPC-E magnetic particle concentrator. Unbound cells were drawn off and the bead pellet was washed twice by resuspension in 1 ml complete medium followed by gentle vortexing. Live unbound cells and bead-bound cells were counted by Trypan blue exclusion.

c. Evaluating sFv Produced from pPhOx.TM Displayed on the Cell Surface.

Figure 3A:
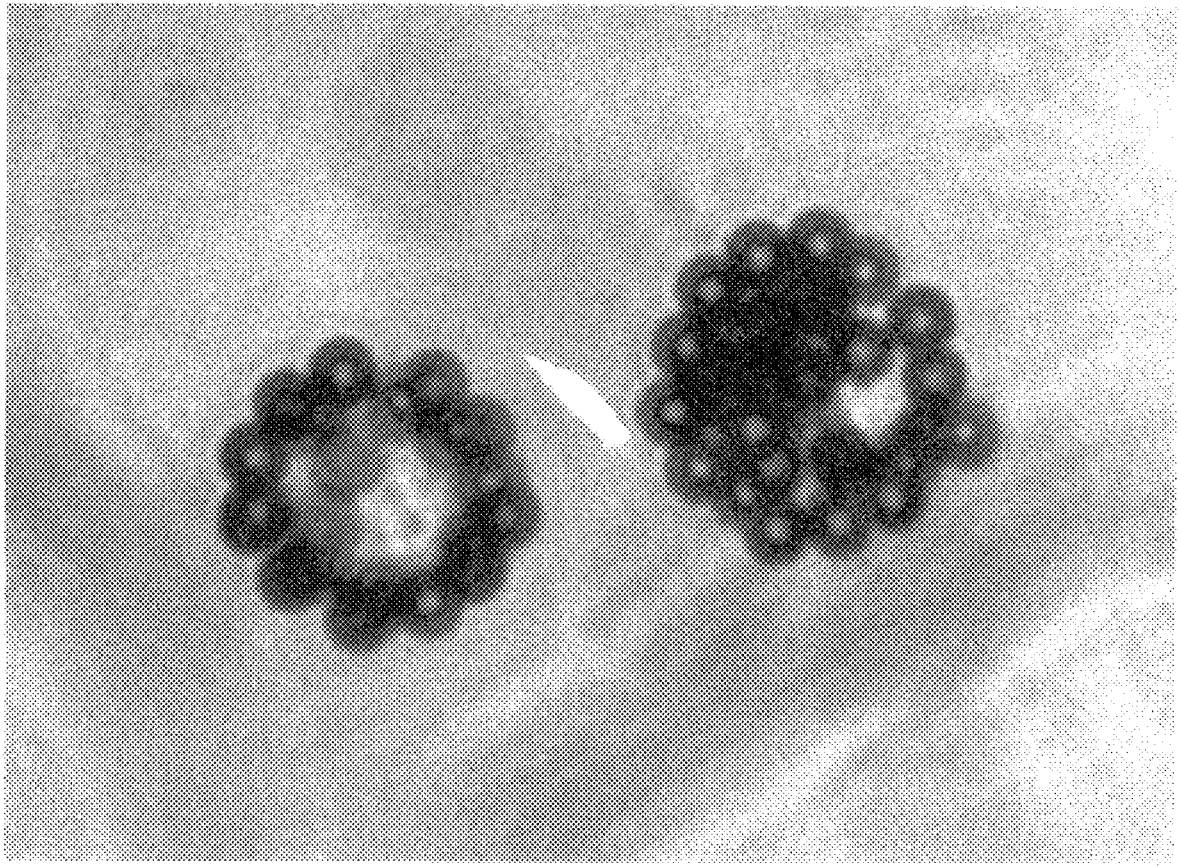
FIG. 3A demonstrates microscopic inspection of adenovirus-transformed human kidney cells, ATCC#CRL-1573 (designated "293") transfected with pPhOx.TM. 24 hours after transfection, the cells were incubated with phOx-BSA magnetic beads for 30 at 37° C. with gentle agitation. Cell binding to antigen (phOx-BSA) coated magnetic beads at 24 hours post-transfection is observed in this micrograph.

To determine whether the sFv produced from pPhOx.TM was successfully displayed on the cell surface, adenovirus-transformed human kidney cells "293" were transfected with either pPhOx.TM or psFv.MUT (which produces a truncated, inactive sFv) and returned to culture for 24 hours. The transiently transfected cell population was harvested and incubated with phOx-BSA magnetic beads for 30 minutes at 37° C. in complete medium with gentle agitation. At the completion of the incubation, bead-bound cells were selected from culture by magnetic interaction. Upon microscopic inspection of the magnetic bead pellet, each selected cell was observed to have bound to it at least one and in many cases several beads. FIG. 3A shows cells at 24 hours post-transfection by electroporation, cells can be observed binding to phOx-BSA coated magnetic beads from culture. None of the cells that had been transfected with psFv.MUT were bound to beads or were selected from culture.

Figure 3B:
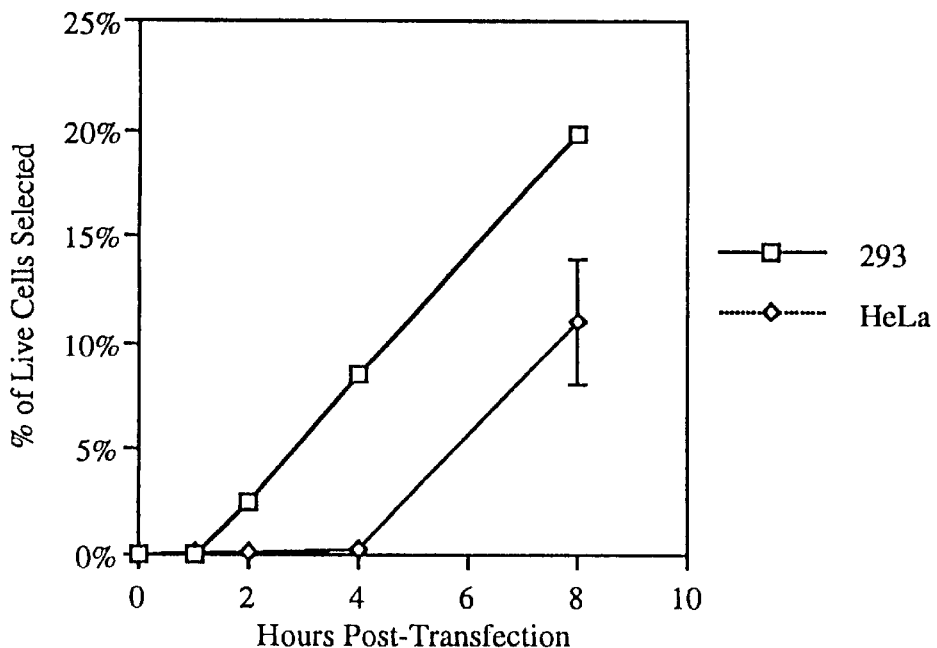
FIG. 3B demonstrates transfected "293" (ATCC #CRL-1573) and HeLa cells (ATCC #CCL-2) transfected with pPhOx.TM by electroporation. "293" cells can be selected from culture as early as two hours post-transfection with pPhOx.TM, indicating that sFv is displayed on the cell surface at two hours post-transfection. HeLa cell display of pPhox sFv did not occur until eight hours post-electroporation (transfection).

A time course of selection was performed in order to demonstrate the ability of the instant invention in selecting transfected cells very soon after introduction of exogenous DNA. In these experiments, "293" (adenovirus transformed human kidney) and HeLa cells were transfected with pPhOx.TM by electroporation. Aliquots of the transiently transfected cell population were incubated with phOx-BSA beads for 30 minutes at 1, 2, 4, and 8 hours post-transfection followed by selection and counting as described. These results, seen in FIG. 3B, show that transiently transfected 293 cells (approximately 2.5% of the surviving population) were selected from the total population as early as 2 hours post-electroporation.

When HeLa cells were transfected in parallel reactions, display of phox sFv sufficient for selection under these conditions occurred at 8 hours post-electroporation. From $2 \times 10^6$ cells in the original population, $1 \times 10^4$ transfected 293 cells were selected at 2 hours and $1 \times 10^4$ HeLa cells were selected at 8 hours. This data is also displayed in FIG. 3B.

Figure 3C:
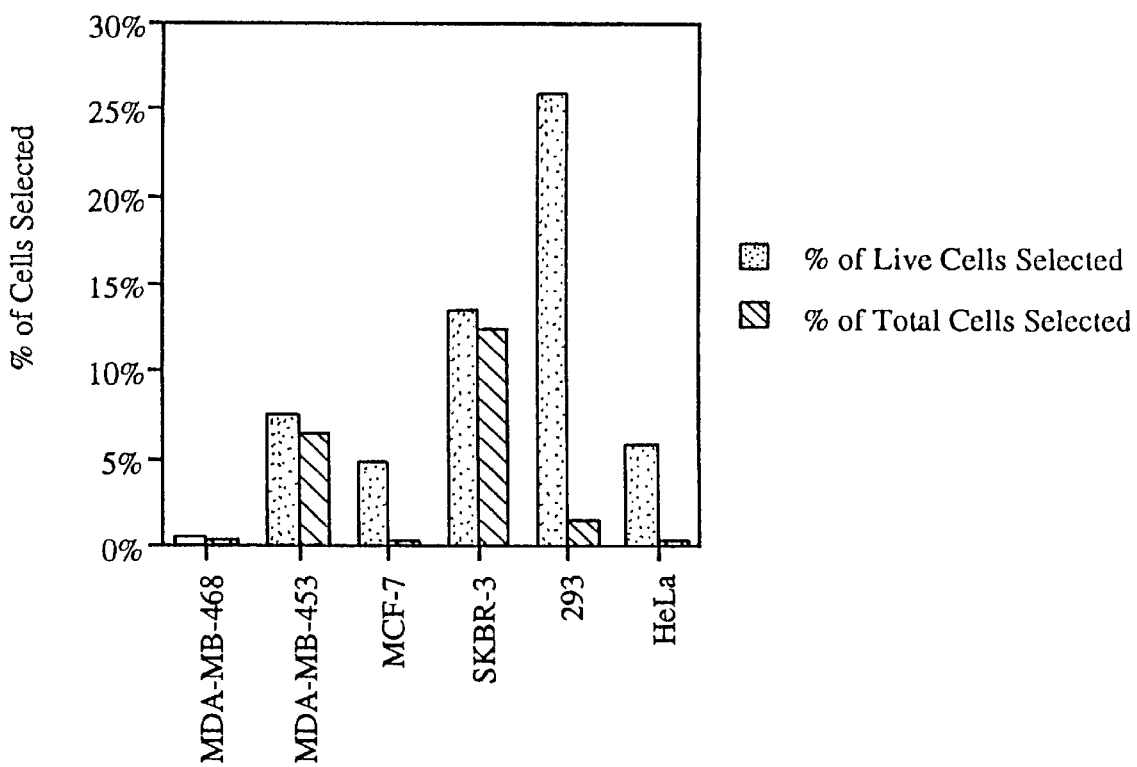
FIG. 3C demonstrates that outer cell membrane expression of sFv can occur in differing cell types. Four cell lines derived from breast tumors and one cell line derived from a malignant melanoma were electroporated with pPhOx.TM and selected with pPhOx-BSA beads at 24 hours. The four breast tumor cell lines, as indicated in Table I, are: (1) MDA-MB-468 (ATCC #HTB-132), a human adenocarcinoma of the breast isolated from pleural effusion, which expresses EGFR; (2) MDA-MB-453 (ATCC #HTB-131), a human adenocarcinoma of the breast isolated from breast effusion, which expresses HER2/neu (3) MCF-7 (ATCC #HTB-22), a human adenocarcinoma of the breast isolated from pleural effusion, which expresses neither EGFR nor HER2/neu; and,(4) SKBR-3 (ATCC #HTB-30), a human adenocarcinoma of the breast isolated from malignant pleural effusion, which expresses both EGFR and HER2/neu. Selected cells were counted and are presented in comparison with the number of cells surviving the electroporation and with the size of the original population ($2 \times 10^6$ cells). Note that selection efficiency varied from cell line to cell line. Increased selection efficiency can be obtained by optimizing transfection conditions for each cell line.

Cell membrane expression of sFV from pPhOx.TM expression can occur in different cell types. pPhOx.TM was introduced into several cell lines including four lines derived from carcinoma of the breast, as summarized in Table I, and adenovirus-transformed human kidney cells designated "293". Cells were selected at 24 hours post-electroporation on phOx-BSA beads and compared for selection efficiency. Under these transfection conditions, all cell lines tested displayed sFv on their membranes sufficient for selection from culture, as graphically displayed in FIG. 3C and Table II. Selection efficiency varied across the cell lines tested. Increased selection efficiency can be obtained by optimizing transfection conditions for specific cells using techniques known to one skilled in the art.

TABLE II

Comparison of expression on phOx sFv and selection efficiencies in cell lines tranfected with pPhOx.TM

| Cell Type | No. Selected | % of Live Cells Selected | % of Total Cells Selected | Mortality |
|---|---|---|---|---|
| MDA-MB-468 | $6.6 \times 10^3$ | 0.4% | 0.3% | 28% |
| MDA-MB-453 | $1.3 \times 10^5$ | 7.5% | 6.5% | 15% |
| MCF-7 | $1.8 \times 10^4$ | 4.8% | 0.1% | 81% |
| SK-BR-3 | $2.5 \times 10^5$ | 13.5% | 12.5% | 8% |
| 293 | $3.1 \times 10^4$ | 25.9% | 1.5% | 94% |
| HeLa | $6.4 \times 10^3$ | 5.9% | 0.3% | 95% |

In parallel reactions, transfected cells were also incubated with magnetic beads coated with BSA alone as a negative control. In each case incubation with BSA beads yielded selection efficiencies of less than 0.03% of the live cells present.

d. Selection Efficiency of Transfected Cells Evaluated by Immunoblot Analysis

As an indication of cell selection efficiency, immunoblot experiments were conducted using samples of transiently transfected cells selected from culture or those that remained unbound to magnetic beads. The presence of sFv in these cell populations was determined using an anti-HA epitope tag antibody 12CA5 (Boehringer Mannheim). MDA-MB-453 and SK-BR-3 cells (see Table I) transfected with pPhOx.TM, described above, were selected from culture at 24 hours post-transfection. Equivalent numbers of untransfected, transfected and selected, or non-selected cells were run on an SDS-polyacrylamide gel (Laemmli, 1970). Separated proteins were transferred to a nitrocellulose membrane and blocked in PBS/0.05% TWEEN-20/5% milk protein (Carnation, Los Angeles, Calif.) for 1 hour at room temperature. Membranes were probed with anti-HA epitope tag antibody, the 12CA5 antibody, by incubating with 12CA5 (Boehringer Mannheim) diluted to 5 μg/ml in blocking buffer for 1 hour at room temperature. The membranes were then washed with PBS/0.05% Tween-20 and incubated with horseradish peroxidase-conjugated goat anti-mouse antibody (BioRad) diluted 1:5000 in blocking buffer for 1 hour at room temperature. Membranes were washed as above, developed using ECL reagents (Amersham) and exposed to film.

Figure 4A:
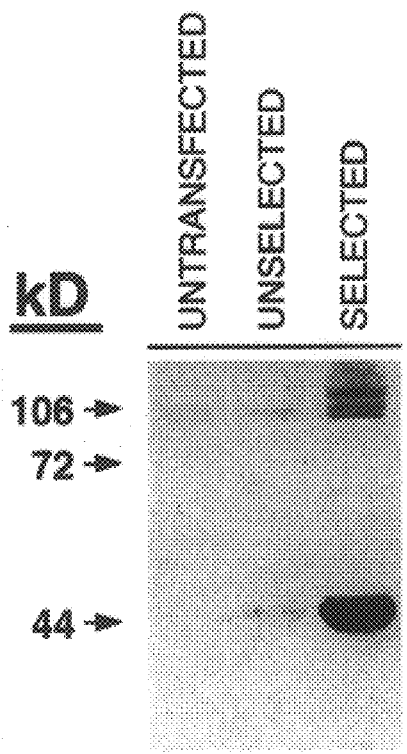
FIGS. 4A and 4B demonstrate that virtually all of the cells that express the sFv fusion protein are efficiently selected from culture using the pPhOx-BSA coated magnetic bead cell selection means. SKBR-3 and MDA-MB-453 cells were transfected and selected with phOx/BSA coated magnetic beads at 24 hours post-transfection. Cellular proteins were then separated by size using an SDS-polyacrylamide gel electrophoresis. The separated proteins were transferred by immunoblot to a nitrocellulose membrane and reacted with radiolabeled antibodies able to bind sFv. Note in the "unselected" lane, meaning cells that did not bind to the magnetic beads, virtually no sFv is detected, indicating that all cells that were transfected were separable from the total cell culture using the cell separation means (the coated magnetic beads).
Figure 4B:
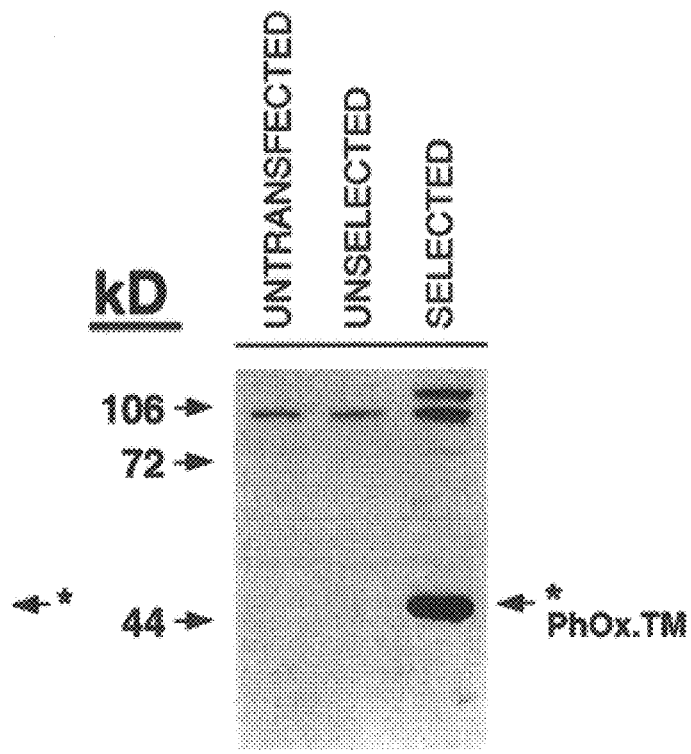

As shown in FIGS. 4A and 4B, virtually all of the immunoreactive sFv appears in the cells that were selected from culture and only a trace of activity remained in the unselected cells. This result suggests that in the two cell lines tested, virtually all of the cells that express the sFv fusion protein are efficiently selected from culture.

e. Coexpression of phox.TM and β-galactosidase in Cotransfected Cells

SK-BR-3 cells were co-transfected with pPhOx.TM and pCMVβ (Clontech) which carries the gene encoding β-galactosidase. Cells were mock transfected or transfected with either 5 μg pPhOx.TM, 5 μg pCMVβ, or 5 μg of each. A non-promoter containing plasmid was used as carrier DNA to make a total of 10 μg in each reaction. One third of each transfection reaction was plated in each chamber of a four chamber microscope slide (Nunc). Slides were incubated at 37° C. for 24 hours then $1 \times 10^5$ cpm of $^{125}$I-phOx-BSA was added to each chamber and allowed to bind for 30 minutes. Slide chambers were then gently washed three times with 1 ml PBS. Cells were then fixed with 1% paraformaldehyde/0.2% glutaraldehyde for 2 minutes and incubated with the colorimetric substrate (5 mM $K_4Fe(CN)_6$, 5 mM $K_3Fe(CN)_6$, 1 mM $MgCl_2$, 0.08% chlorobromo-indolyl β-D galactopyranoside, X-gal, Sigma) for β-galactosidase activity for 15 hours at 27° C. The slides were washed with PBS and the cells dehydrated by successive 5 minute washes in 50%, 75%, and 100% ethanol and air dried. They were then coated with photographic emulsion (NTB-3, Kodak) and dried overnight. Coated slides were exposed at 4° C. for four days and developed using Kodak developing solutions. In addition, 1 ml of each transfection reaction was incubated with phOx-BSA beads as described in Example III(b) above. The selected cells were then stained for β-galactosidase activity.

$^{125}$I-phOx-BSA was prepared by combining 100 μg BSA protein and 500 μCi $Na^{125}$I (Dupont/NEN, Boston, Mass.) to iodogen-coated tubes using the manufacturer's protocol (Pierce). Free $^{125}$I was removed by applying reactions to an ECONO-PAC 10DG column (BioRad) that had been blocked with BSA and equilibrated in PBS. Labeled protein was eluted in PBS.

Figures 5A, 5B:
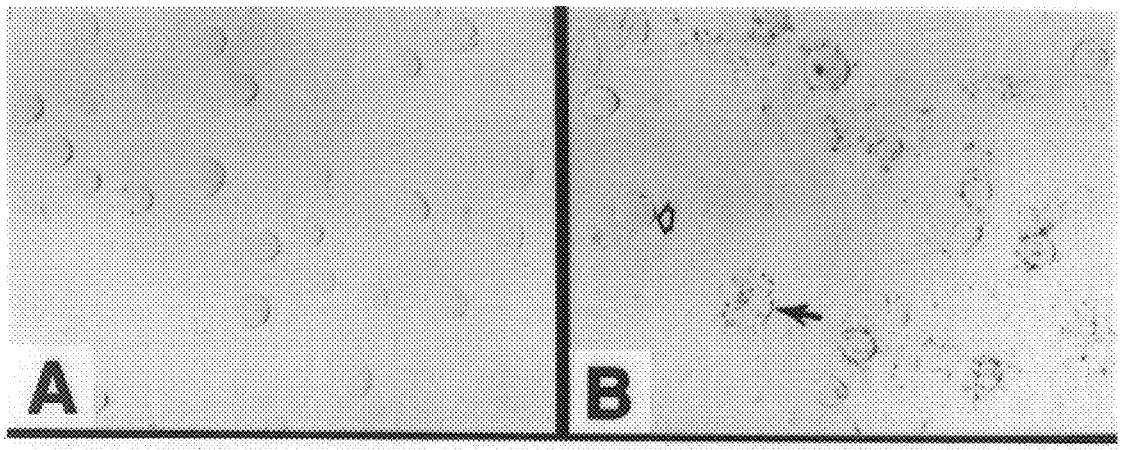
FIGS. 5A–5D demonstrate the efficiency of coexpression of pPhOx.TM and beta-galactosidase. SKBR-3 cells were co-transfected with pPhOx.TM and a vector expressing the gene for β-galactosidase, named pCMVβ, (Clontech, Palo Alto, Calif). One third of each transfection reaction was plated in each chamber of a four chamber microscope slide (Nunc, Napierville, Ill.). Details of the experiment are described in Example III (e) below. Panel A shows mock transfected cells; panel B shows cells transfected with pPhOx.TM alone; panel C shows cells transfected with pCMVβ (β-galactosidase expressing; and panel D shows cells transfected with both pPhOx.TM and pCMVβ.
Figures 5C, 5D:
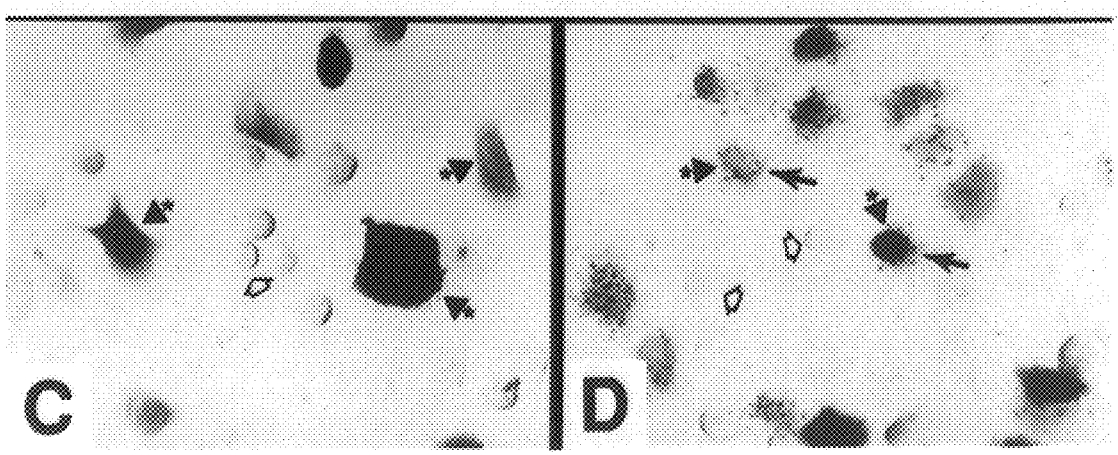

The results, depicted in the radiograph/photograph of FIGS. 5 A–D, demonstrate that most if not all of the cells expressing the functional pPhOx.TM product (cells with silver grains, denoted by arrows) are also expressing β-galactosidase (blue staining, the point of the triangles opposite the stars points towards representative cells staining for β-galactosidase). The data demonstrates that greater than 98% of the cells selected with phox-BSA-coated magnetic beads stained positively for β-galactosidase activity.

EXAMPLE IV

General Procedure for Co-Transfection with PhOx.TM Vector and Second Plasmid Containing Gene of Interest A. Plasmid Preparation In order to insure that the plasmid DNA used in the instant procedure is of high quality and free of contaminants, the PhOx.TM vector and the vector containing the gene of interest was subjected to CsCl gradient ultracentrifugation. Boiled or alkaline lysis miniprep DNA should not be used in this procedure. Further purification methods can be found in Ausubel, F. M., Brent, R., Kingston, R. E., Moore, D. D., Seidman, J. G., Smith, J. A., Struhl, K., eds (1990) *Current Protocols in Molecular Biology*. Greene Publishing Associates and Wiley-Interscience, New York.

In addition, the PhOx.TM Vector can be amplified prior to use in the instant invention by transforming the plasmid into a recA, endA *E. coli* (e.g. DH5α) strain. The lyophilized vector is resuspended in 20 μl of sterile water to make a stock solution. A small portion (1 μl) of the stock solution can be used to transfect the *E. coli* of choice on LB plates containing 100 μg/ml ampicillin or 50 μg/ml kanamycin.

B. Positive Control

The pCR™3lacZ (8.1 kb) plasmid used in this procedure as a positive control is constructed by inserting the lacZ gene in the EcoR1 cite of the pCR™3 plasmid (Invitrogen, San Diego, Calif.). The positive control serves to assist in optimizing the transfection conditions for the PhOx.TM and co-tranfected vectors. The pCR™3lacZ contains the *E. coli* gene encoding β-galactosidase, which gene is expressed in mammalian cells using the immediate-early promoter from cytomegalovirus. A successful cotransfection with the PhOx.TM or the vector bearing the gene of interest will result in positive β-galactosidase expression in selected cells and can be easily monitored with a calorimetric b-galactosidase assay, as described below.

C. Methods of Transfection

Transfection procedures for the cell line of interest may often be found in articles discussing that particular cell line. Such methods of transfections are well known and may include calcium phosphate, DEAE-dextran, liposome-mediated, or electroporation. The protocol discussed in the art for the cell line of interest should be followed exactly. Particular attention should be paid to medium requirements, when to pass the cells, and at what dilution to split the cells. Further information can be found in *Current Protocols in Molecular Biology. supra.*

In the event that the art does not teach a transfection method for the cell line of interest, electroporation is the method of choice. For instance, the following electroporation protocol may be used (a "no DNA" negative control should also be used):

1. Prepare Trypsin/versene (EDTA) or PBS/3 mM EDTA. The latter can be prepared as follows:
   137 mM NaCl
   2.7 mM KCl
   10 mM $Na_2HPO_4$
   1.8 mM $KH_2PO_4$
   (3 mM EDTA, optional)
   a. Dissolve: 8 g NaCl
      0.2 g KCl
      1.44 g $Na_2HPO_4$
      0.24 g $KH_2PO_4$
      (6 ml 0.5 M EDTA, pH 8)
      in 800 ml deionized water.
   b. Adjust the pH to 7.4 with concentrated HCl.
   c. Bring the volume to 1 liter and autoclave for 20 minutes on liquid cycle.

d. Store at +4° C. or room temperature.
2. Change medium on the cells 24 hours prior to electroporation.
3. Harvest the cells at 60–80% confluency using half of the initial culture volume of PBS/3 mM EDTA.
4. Count the cells and resuspend them in complete medium at $1 \times 10^7$ cells/ml.
5. Mix PhOx.TM and the construct containing the gene of interest (or pCR3lacZ) in a 1:1 molar ratio in a volume of 10 μl or less. Use 1–5 μg of each plasmid.
6. The plasmid mixture is added to 200 μl of the cell suspension ($2 \times 10^6$ cells). The suspension is mixed gently and is transferred to a chilled electroporation cuvette (0.4 cm gap width).
7. The cells are electroporated using the recommended settings of the electroporation device.
8. The electroporated cells are transferred to a 60 mm plate containing 5–7 ml complete medium. The plates are incubated in a 37° C., 5% $CO_2$ incubator for 2–48 hours.

D. Cell Selection

The transfected cells from the above Section C can be isolated using the following procedure. In general, the procedure employs $1.5 \times 10^6$ beads per 60 mm plate of transfected cells. These conditions may vary due to the method of transfection and the cell line used. Sterile techniques should be used when performing the following steps.
1. Preparation of Transfected Cells
The PBS/3 mM EDTA buffer described above and complete medium should be prepared before attempting the following steps:
  a. PBS/3 mM EDTA (3–5 ml) is added to the cells. The cells are incubated for 5 minutes at 37° C. and then are harvested. Untransfected cells (or the cells from the negative transfection control) may be harvested for use as a negative control when assaying for b-galactosidase activity.
  b. The cells are centrifuged at 800–1000 xg for 5–10 minutes at room temperature. The supernatant is decanted.
  c. The cells are resuspended in 1 ml complete medium per 60 mm plate. The cells are pipetted up and down in order to break up cell clumps and achieve a single-cell suspension.
2. Preparation of Magnetic Beads
The magnetic beads are washed before use to remove any sodium azide present.
  d. A microcentrifuge tube is prepared for each 60 mm plate of cells.
  e. The magnetic beads slurry is vortexed to resuspend beads and is added (10 μl ($1.5 \times 10^6$ beads)) into each microcentrifuge tube.
  f. The beads are washed by adding 1 ml complete medium to each tube and are mixed by inversion 3 times. The beads are pelleted with a strong magnet or magnetic stand and the medium is removed by pipetting or aspiration.
3. Selection of Transfected Cells
  g. Cell suspension (1 ml) from Step 1C is added to a tube containing washed beads from Step 2f. The suspension is incubated for 30 minutes.
  h. The tubes containing the bead-cell mixture are placed in a magnetic stand and are mixed for 30 seconds to 1 minute with a gentle end over end rotation.
  i. While the tube is still in contact with the magnet, the non-selected cells are removed with a pipet. (These cells may be saved for further analysis.)
  j. The tubes are removed from the magnetic stand and the beads and cells are resuspended in 1 ml complete medium. The suspension is vortexed gently.
  k. The beads (and bound cells) are pelleted using the magnetic stand, the supernatant is removed by pipet.
  l. Repeat Steps j and k two more times.
  m. Selected cells are resuspended in 100 μl complete medium (for pCR™3lacZ control, use X-gal Reagent, see below) and the cells are counted. The cells are ready to culture or analyze.

E. Optimization of Cell Transfection

The first step in utilizing the method of this invention can be to optimize the transfection conditions for the cell line of interest. Once transfection conditions have been optimized, the cell line can then be cotransfected with the PhOx.TM vector and the vector containing the gene of interest.

The pCR™3lacZ positive control plasmid can be used to check for cotransfection of selected cells and assessing transfection efficiencies. Transfected cells are selected using the above methods. Untransfected cells, selected cells, and non-selected cells are assayed with X-gal and counted. (Cells expressing b-galactosidase will turn blue in the presence of X-gal.) Comparison of the number of blue, non-selected cells versus blue, selected cells will allow the determinination of selection efficiency. (Untransfected cells should not stain with X-gal.) Optimal cotransfection conditions are defined as when the PhOx.TM to pCR™3lacZ ratio gives the greatest enrichment of blue-stained cells in the selected population.
1. Preparation of X-gal Reagent
  1 mg/ml X-Gal in DMF
  4 mM potassium ferricyanide ($K_3Fe(CN)_6$)
  4 mM potassium ferrocyanide ($K_4Fe(CN)_6 \cdot 3H_2O$)
  2 mM magnesium chloride hexahydrate in PBS, pH 7.4
  a. Each of the following stock solutions (10 ml) are prepared. These solutions are stable indefinitely if stored as indicated.
    X-gal: (20 mg/ml in dimethylformamide (DMF)): Dissolve 200 mg of X-gal in 10 ml DMF and store at −20° C.
    Potassium Ferricyanide and Potassium Ferrocyanide: (0.4 M each in deionized water.): Dissolve 1.32 g of potassium ferricyanide and 1.69 g of potassium ferrocyanide in 10 ml deionized water. Store at −20° C.
    Magnesium Chloride: (200 mM in deionized water.): Dissolve 0.4 g in 10 ml deionized water and store at room temperature or −20° C.
  b. For 10 ml of X-gal reagent, mix together:
    0.5 ml of 20 mg/ml X-Gal stock solution;
    0.1 ml of the potassium ferricyanide/ferrocyanide stock solution;
    0.1 ml of the magnesium chloride stock solution; and
    9.3 ml of PBS.
2. Colorimetric Assay for β-galactosidase
  a. To Assay Selected Cells:
    i. The selected cells are resuspended in 100 μl X-gal Reagent:
    ii. The cells are incubated overnight at room temperature:
    iii. The cells are examined under the microscope for the development of blue color and the number of stained and total cells is counted.

b. To Assay Non-selected Cells:
  i. The non-selected cells are centrifuged 5 minutes at 4000 rpm to pellet the cells. The supernatant is decanted.
  ii. The cells are resuspended in 1 ml PBS and again pelleted. The supernatant is decanted.
  iii. The cells are resuspended in 100 µl of X-gal Reagent and are incubated overnight at room temperature.
  iv. The cells are examined under a microscope for the development of blue color. The number of total cells and blue cells are counted.
c. To Assay Untransfected Cells (Negative Control):
  i. The untransfected cells are centrifuged for 5 minutes at 4000 rpm to pellet the cells.
  ii. The cells are resuspended in 1 ml PBS and recentrifuged in order to pellet the cells.
  iii. The cells are resuspended in 100 µl of X-gal Reagent and are incubated overnight at room temperature.
  iv. The cells are examined under a microscope for the development of blue color. The number of total cells and blue cells are counted.

In all of the above counting procedures the total cell number is normalized.

F. Optimization of Cell Selection

The presence of unbound beads after the application of the magnet to the transfection mixture indicates that a proper number of magnetic beads. If no unbound beads are observed, it may mean that not all tranfected cells were selected in the procedure. Should the procedure using those particular conditions be repeated, it is desirable to double the number of beads (e.g., 20 µl or $3 \times 10^6$ beads) in order to ensure that you isolate all transfected cells.

In the transfection optimization procedure, nearly all selected cells should express β-galactosidase. If there are non-selected cells that are blue, then the relative amount of PhOx.TM to pCR™3lacZ should be increased.

Although the invention has been described with reference to the examples provided above, it should be understood that various modifications can be made by those skilled in the art without departing from the invention. Accordingly, the invention is set out in the following claims.

We claim:

1. A eukaryotic expression vector for the identification and separation of transfected cells from a total cell population, comprising:
   a first DNA sequence encoding an anti-hapten single-chain antibody, which antibody binds to a specific hapten, wherein said hapten is 4-ethoxymethylene-2-phenyl-2-oxazolin-5-one;
   a second DNA sequence encoding a transmembrane domain, wherein said second DNA sequence is functionally linked to said first DNA sequence;
   a third DNA sequence encoding a signal sequence, wherein said third DNA sequence is functionally linked to said first DNA sequence;
   a first promoter operatively linked to said first DNA sequence;
   at least one additional DNA sequence encoding at least one protein; and
   a second promoter operatively linked to said additional DNA sequence.

2. A kit for the identification and separation of transfected cells from a total cell population, comprising:
   a cell separation means and a eukaryotic expression vector, wherein said vector comprises:
     a first DNA sequence encoding an anti-hapten single-chain antibody, which antibody binds to a specific hasten wherein said hapten is 4-ethoxymethylene-2-pehnyl-2-oxazolin-5-one;
     a second DNA sequence encoding a transmembrane domain, wherein said second DNA sequence is functionally linked to said first DNA sequence;
     a third DNA sequence encoding a signal sequence, wherein said third DNA sequence is functionally linked to said first DNA sequence;
     a first promoter operatively linked to said first DNA sequence;
     at least one additional DNA sequence encoding at least one protein; and
     a second promoter operatively linked to said additional DNA sequence.

3. The kit of claim 2, wherein said cell separation means comprises magnetic beads.

4. The kit of claim 3, wherein said cell separation means further comprises magnetic beads coated with a hapten.

5. A method of identifying and isolating transfected cells from a total cell population, comprising:
   (a) transfecting a eukaryotic cell in culture with a eukaryotic expression vector, wherein said vector comprises:
     a first DNA sequence encoding an anti-hapten signal-chain antibody, which antibody binds to a specific hapten;
     a second DNA sequence encoding a transmembrane domain, wherein said second DNA sequence is functionally linked to said first DNA sequence;
     a third DNA sequence encoding a signal sequence, wherein said third DNA sequence is functionally linked to said first DNA sequence;
     a first promoter operatively linked to said first DNA sequence;
     at least one additional DNA sequence encoding at least one protein; and
     a second promoter operatively linked to said additional DNA sequence;

(b) exposing said cell to a hapten conjugated to a cell selection means; and (c) separating said cell, bound to said selection means, from the total cell population.

6. The method of claim 5, wherein said hapten is 4-ethoxymethylene-2-phenyl-2-oxazolin-5-one.

7. The method of claim 5, wherein said vector is selected from the group consisting of a plasmid, a virus or double-stranded DNA.

8. The method of claim 5, wherein said transmembrane domain comprises an immunoglobulin or a platelet derived growth factor transmembrane domain.

9. The method of claim 5, wherein said signal sequence comprises a murine immunoglobulin kappa chain V-J2-C region signal peptide.

10. The method of claim 5, wherein said first promoter comprises cytomegalovirus (CMV) immediate early promoter, Rous sarcoma virus (RSV) promoter, adenovirus major late promoter, SV40 early promoter or retroviral long terminal repeats (LTRs).

11. The method of claim 5, wherein said single-chain antibody is expressed extracellularly at least two hours after transfection.

12. The method of claim 5, wherein said transfecting of said cell is effected by electroporation.

13. The method of claim 5, wherein said separating of said cell is effected by physical separation.

14. The method of claim 5, wherein said cell separation means comprises magnetic beads.

15. A method of identifying and isolating transfected cells from a total cell population, comprising:

(a) transfecting a eukaryotic cell in culture with a mixture of eukaryotic expression vectors comprising a first vector, wherein said first vector comprises:

a first DNA sequence encoding an anti-hapten single-chain antibody, which antibody binds to a specific hapten;

a second DNA sequence encoding a transmembrane domain, wherein said second DNA sequence is functionally linked to said first DNA sequence;

a third DNA sequence encoding a signal sequence, wherein said third DNA sequence is functionally linked to said first DNA sequence;

a first promoter operatively linked to said first DNA sequence;

at least one additional DNA sequence encoding at least one protein; and a second promoter operatively linked to said additional DNA sequence;

(b) exposing said cell to a hapten conjugated to a cell selection means; and (c) separating said cell, bound to said selection means, from the total cell population.

16. The method of claim 15, wherein said hapten is 4-ethoxymethylene-2-phenyl-2-oxazolin-5-one.

17. The method of claim 15, wherein said vector is selected from the group consisting of a plasmid, a virus or double-stranded DNA.

18. The method of claim 15, wherein said transmembrane domain comprises an immungloubulin or a platelet derived growth factor transmembrane domain.

19. The method of claim 15, wherein said signal sequence comprises a murine immunoglobulin kappa chain V-J2-C region signal peptide.

20. The method of claim 15, wherein said promoter comprises cytomegalovirus (CMV) immediate early promoter, Rous sarcoma virus (RSV) promoter, adenovirus major late promoter, SV40 early promoter or viral long terminal repeats (LTRs).

21. The method of claim 15, wherein said single-chain antibody is expressed extracellularly at least two hours after transfection.

22. The method of claim 15, wherein said transfecting of said cell is effected by electroporation.

23. The method of claim 15, wherein said separating of said cell is effected by physical separation.

24. The method of claim 15, wherein said cell separation means comprises magnetic beads.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 1555 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1130..1180
        (D) OTHER INFORMATION: /note= "N=Unknown or Other"

(xi) SEQUENCE DESCRIPTION: SEQ ID NO:1:

```
GCGCGCGTTG ACATTGATTA TTGACTAGTT ATTAATAGTA ATCAATTACG GGGTCATTAG     60

TTCATAGCCC ATATATGGAG TTCCGCGTTA CATAACTTAC GGTAAATGGC CCGCCTGGCT    120

GACCGCCCAA CGACCCCCGC CCATTGACGT CAATAATGAC GTATGTTCCC ATAGTAACGC    180

CAATAGGGAC TTTCCATTGA CGTCAATGGG TGGACTATTT ACGGTAAACT GCCCACTTGG    240

CAGTACATCA AGTGTATCAT ATGCCAAGTA CGCCCCCTAT TGACGTCAAT GACGGTAAAT    300

GGCCCGCCTG GCATTATGCC CAGTACATGA CCTTATGGGA CTTTCCTACT TGGCAGTACA    360

TCTACGTATT AGTCATCGCT ATTACCATGG TGATGCGGTT TTGGCAGTAC ATCAATGGGC    420

GTGGATAGCG GTTTGACTCA CGGGGATTTC CAAGTCTCCA CCCCATTGAC GTCAATGGGA    480

GTTTGTTTTG GCACCAAAAT CAACGGGACT TTCCAAAATG TCGTAACAAC TCCGCCCCAT    540

TGACGCAAAT GGGCGGTAGG CGTGTACGGT GGGAGGTCTA TATAAGCAGA GCTCTCTGGC    600

TAACTAGAGA ACCCACTGCT TACTGGCTTA TCGAAATTAA TACGACTCAC TATAGGGAGA    660

CCCAAGCTTG GTACCGAGCT CGGATCCACT AGTAACGGCC GCCAGTGTGC TGGAATTCGG    720

CTTGGGGATA TCCACCATGG AGACAGACAC ACTCCTGCTA TGGGTACTGC TGCTCTGGGT    780

TCCAGGTTCC ACTGGTGACT ATCCATATGA TGTTCCAGAT TATGCTGGGG CCCAGCCGGC    840
```

```
CATGGCCGAG GTCAAGCTGC AGGAGTCAGG GGGAGGCTTA GTGCAGCCTG GAGGGTCCCG      900

GAAACTCTCC TGTGCAGCCT CTGGATTCAC TTTCAGTAGC TTTGGAATGC ACTGGGTTCG      960

TCAGGCTCCA GAGAAGGGGC TGGAGTGGGT CGCATATATT AGTAGTGGCA GTAGTACCAT     1020

CTACTATGCA GACACAGTGA AGGGACGATT CACCATCTCC AGAGACAATC CAAGAACAC      1080

CCTGTTCCTG CAAATGACCA GTCTAAGGTC TGAGGACACG GNCATGTATT ACTGTGCAAG     1140

AGATTACGGG GCTTATTGGG GCCAAGGGAC CACGGNCACC GTCTCCTCAG GTGGAGGCGG     1200

CTCAGGCGGA GGTGGCTCTG GCGGTGGCGG ATCGGACATT GAGCTCACCC AGTCTCCAGC    1260

AATCATGTCT GCATCTCCAG GGGAGAGGGT CACCATGACC TGCAGTGCCA GTTCAAGTGT    1320

AAGGTACATG AACTGGTTCC AACAGAAGTC AGGCACCTCC CCCAAAAGAT GGATTTATGA    1380

CACATCCAAA CTGTCTTCTG GAGTCCCTGC TCGCTTCAGT GGCAGTGGGT CTGGGACCTC    1440

TTACTCTCTC ACAATCAGCA GCATGGAGGC TGAAGATGCT GCCACTTACT ACTGCCAGCA    1500

GTGGAGTAGT AACCCACTCA CGTTCGGTGC TGGGACCAAG CTGGAGCTGA AACGG          1555

(2) INFORMATION FOR SEQ ID NO:2:

(i) SEQUENCE CHARACTERISTICS:
        (A) LENGTH: 4557 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GCGGCCGCAG AACAAAAACT CATCTCAGAA GAGGATCTGA ATGGGGCCGT CGACGAACAA       60

AAACTCATCT CAGAAGAGGA TCTGAATGCT GTGGGCCAGG ACACGCAGGA GGTCATCGTG      120

GTGCCACACT CCTTGCCCTT TAAGGTGGTG GTGATCTCAG CCATCCTGGC CCTGGTGGTG      180

CTCACCATCA TCTCCCTTAT CATCCTCATC ATGCTTTGGC AGAAGAAGCC ACGTTAGGCG      240

GCCGCTCGAG CATGCATCTA GAGGGCCCTA TTCTATAGTG TCACCTAAAT GCTAGAGCTC      300

GCTGATCAGC CTCGACTGTG CCTTCTAGTT GCCAGCCATC TGTTGTTTGC CCCTCCCCCG      360

TGCCTTCCTT GACCCTGGAA GGTGCCACTC CCACTGTCCT TTCCTAATAA AATGAGGAAA      420

TTGCATCGCA TTGTCTGAGT AGGTGTCATT CTATTCTGGG GGGTGGGGTG GGCAGGACA       480

GCAAGGGGGA GGATTGGGAA GACAATAGCA GGCATGCTGG GGATGCGGTG GGCTCTATGG      540

CTTCTGAGGC GGAAAGAACC AGTGGCGGTA ATACGGTTAT CCACAGAATC AGGGGATAAC      600

GCAGGAAAGA ACATGTGAGC AAAAGGCCAG CAAAAGGCCA GGAACCGTAA AAAGGCCGCG      660

TTGCTGGCGT TTTTCCATAG GCTCCGCCCC CCTGACGAGC ATCACAAAAA TCGACGCTCA      720

AGTCAGAGGT GGCGAAACCC GACAGGACTA TAAAGATACC AGGCGTTTCC CCCTGGAAGC      780

TCCCTCGTGC GCTCTCCTGT TCCGACCCTG CCGCTTACCG GATACCTGTC CGCCTTTCTC      840

CCTTCGGGAA GCGTGGCGCT TTCTCATAGC TCACGCTGTA GGTATCTCAG TTCGGTGTAG      900

GTCGTTCGCT CCAAGCTGGG CTGTGTGCAC GAACCCCCCG TTCAGCCCGA CCGCTGCGCC      960

TTATCCGGTA ACTATCGTCT TGAGTCCAAC CCGGTAAGAC ACGACTTATC GCCACTGGCA     1020

GCAGCCACTG GTAACAGGAT TAGCAGAGCG AGGTATGTAG GCGGTGCTAC AGAGTTCTTG     1080

AAGTGGTGGC CTAACTACGG CTACACTAGA AGGACAGTAT TTGGTATCTG GCTCTGCTG     1140

AAGCCAGTTA CCTTCGGAAA AAGAGTTGGT AGCTCTTGAT CCGGCAAACA AACCACCGCT     1200

GGTAGCGGTG GTTTTTTTGT TTGCAAGCAG CAGATTACGC GCAGAAAAAA AGGATCTCAA     1260
```

-continued

```
GAAGATCCTT TGATCTTTTC TACGGGTCT GACGCTCAGT GGAACGAAAA CTCACGTTAA      1320

GGGATTTTGG TCATGAGATT ATCAAAAAGG ATCTTCACCT AGATCCTTTT AAATTAAAAA      1380

TGAAGTTTTA AATCAATCTA AAGTATATAT GAGTAACCTG AGGCTATGGC AGGGCCTGCC      1440

GCCCCGACGT TGGCTGCGAG CCCTGGGCCT TCACCCGAAC TTGGGGGGTG GGGTGGGGAA      1500

AAGGAAGAAA CGCGGGCGTA TTGGCCCCAA TGGGGTCTCG GTGGGGTATC GACAGAGTGC      1560

CAGCCCTGGG ACCGAACCCC GCGTTTATGA ACAAACGACC CAACACCGTG CGTTTTATTC      1620

TGTCTTTTTA TTGCCGTCAT AGCGCGGGTT CCTTCCGGTA TTGTCTCCTT CCGTGTTTCA      1680

GTTAGCCTCC CCCTAGGGTG GGCGAAGAAC TCCAGCATGA GATCCCCGCG CTGGAGGATC      1740

ATCCAGCCGG CGTCCCGGAA AACGATTCCG AAGCCCAACC TTTCATAGAA GGCGGCGGTG      1800

GAATCGAAAT CTCGTGATGG CAGGTTGGGC GTCGCTTGGT CGGTCATTTC GAACCCCAGA      1860

GTCCCGCTCA GAAGAACTCG TCAAGAAGGC GATAGAAGGC GATGCGCTGC GAATCGGGAG      1920

CGGCGATACC GTAAAGCACG AGGAAGCGGT CAGCCCATTC GCCGCCAAGC TCTTCAGCAA      1980

TATCACGGGT AGCCAACGCT ATGTCCTGAT AGCGGTCCGC CACACCCAGC CGGCCACAGT      2040

CGATGAATCC AGAAAAGCGG CCATTTTCCA CCATGATATT CGGCAAGCAG GCATCGCCAT      2100

GGGTCACGAC GAGATCCTCG CCGTCGGGCA TGCTCGCCTT GAGCCTGGCG AACAGTTCGG      2160

CTGGCGCGAG CCCCTGATGC TCTTGATCAT CCTGATCGAC AAGACCGGCT TCCATCCGAG      2220

TACGTGCTCG CTCGATGCGA TGTTTCGCTT GGTGGTCGAA TGGGCAGGTA GCCGGATCAA      2280

GCGTATGCAG CCGCCGCATT GCATCAGCCA TGATGGATAC TTTCTCGGCA GGAGCAAGGT      2340

GAGATGACAG GAGATCCTGC CCCGGCACTT CGCCCAATAG CAGCCAGTCC CTTCCCGCTT      2400

CAGTGACAAC GTCGAGCACA GCTGCGCAAG GAACGCCCGT CGTGGCCAGC CACGATAGCC      2460

GCGCTGCCTC GTCTTGCAGT TCATTCAGGG CACCGGACAG GTCGGTCTTG ACAAAAAGAA      2520

CCGGGCGCCC CTGCGCTGAC AGCCGGAACA CGGCGGCATC AGAGCAGCCG ATTGTCTGTT      2580

GTGCCCAGTC ATAGCCGAAT AGCCTCTCCA CCCAAGCGGC CGGAGAACCT GCGTGCAATC      2640

CATCTTGTTC AATCATGCGA AACGATCCTC ATCCTGTCTC TTGATCGATC TTTGCAAAAG      2700

CCTAGGCCTC CAAAAAAGCC TCCTCACTAC TTCTGGAATA GCTCAGAGGC CGAGGCGGCT      2760

TCGGCCTCT GCATAAATAA AAAAAATTAG TCAGCCATGG GGCGGAGAAT GGGCGGAACT      2820

GGGCGGAGTT AGGGGCGGGA TGGGCGGAGT TAGGGGCGGG ACTATGGTTG CTGACTAATT      2880

GAGATGCATG CTTTGCATAC TTCTGCCTGC TGGGGAGCCT GGGGACTTTC CACACCTGGT      2940

TGCTGACTAA TTGAGATGCA TGCTTTGCAT ACTTCTGCCT GCTGGGGAGC CTGGGGACTT      3000

TCCACACCCT AACTGACACA CATTCCACAG CTGGTTCTTT CCGCCTCAGG ACTCTTCCTT      3060

TTTCAATAAA TCAATCTAAA GTATATATGA GTAAACTTGG TCTGACAGTT ACCAATGCTT      3120

AATCAGTGAG GCACCTATCT CAGCGATCTG TCTATTTCGT TCATCCATAG TTGCCTGACT      3180

CCCCGTCGTG TAGATAACTA CGATACGGGA GGGCTTACCA TCTGGCCCCA GTGCTGCAAT      3240

GATACCGCGA GACCCACGCT CACCGCTCCA GATTTATCAG CAATAAACCA GCCCAGCCGG      3300

AAGGGCCGAG CGCAGAAGTG GTCCTGCAAC TTTATCCGCC TCCATCCAGT CTATTAATTG      3360

TTGCCGGGAA GCTAGAGTAA GTAGTTCGCC AGTTAATAGT TTGCGCAACG TTGTTGCCAT      3420

TGCTACAGGC ATCGTGGTGT CACGCTCGTC GTTTGTATGG CTTCATTCAG CTCCCGGTTC      3480

CCAACGATCA AGGCGAGTTA CATGATCCCC CATGTTGTGC AAAAAAGCGG TTAGCTCCTT      3540

CGGTCCTCCG ATCGTTGTCA GAAGTAAGTT GGCCGCAGTG TTATCACTCA TGGTTATGGC      3600

AGCACTGCAT AATTCTCTTA CTGTCATGCC ATCCGTAAGA TGCTTTTCTG TGACTGGTGA      3660
```

-continued

| | |
|---|---|
| GTACTCAACC AAGTCATTCT GAGAATAGTG TATGCGGCGA CCGAGTTGCT CTTGCCCGGC | 3720 |
| GTCAATACGG GATAATACCG CGCCACATAG CAGAACTTTA AAAGTGCTCA TCATTGGAAA | 3780 |
| ACGTTCTTCG GGGCGAAAAC TCTCAAGGAT CTTACCGCTG TTGAGATCCA GTTCGATGTA | 3840 |
| ACCCACTCGT GCACCCAACT GATCTTCAGC ATCTTTTACT TTCACCAGCG TTTCTGGGTG | 3900 |
| AGCAAAAACA GGAAGGCAAA ATGCCGCAAA AAAGGGAATA AGGGCGACAC GGAAATGTTG | 3960 |
| AATACTCATA CTCTTCCTTT TTCAATATTA TTGAAGCATT TATCAGGGTT ATTGTCTCAT | 4020 |
| GAGCGGATAC ATATTTGAAT GTATTTAGAA AAATAAACAA ATAGGGGTTC CGCGCACATT | 4080 |
| TCCCCGAAAA GTGCCACCTG ACGCGCCCTG TAGCGGCGCA TTAAGCGCGG CGGGTGTGGT | 4140 |
| GGTTACGCGC AGCGTGACCG CTACACTTGC CAGCGCCCTA GCGCCCGCTC CTTTCGCTTT | 4200 |
| CTTCCCTTCC TTTCTCGCCA CGTTCGCCGG CTTTCCCCGT CAAGCTCTAA ATCGGGGGCT | 4260 |
| CCCTTTAGGG TTCCGATTTA GTGCTTTACG GCACCTCGAC CCCAAAAAAC TTGATTAGGG | 4320 |
| TGATGGTTCA CGTAGTGGGC CATCGCCCTG ATAGACGGTT TTTCGCCCTT TGACGTTGGA | 4380 |
| GTCCACGTTC TTTAATAGTG GACTCTTGTT CCAAACTGGA ACAACACTCA ACCCTATCTC | 4440 |
| GGTCTATTCT TTTGATTTAT AAGGGATTTT GCCGATTTCG GCCTATTGGT TAAAAAATGA | 4500 |
| GCTGATTTAA CAAAAATTTA ACGCGAATTT TAACAAAATA TTAACGCTTA CAATTAC | 4557 |

(2) INFORMATION FOR SEQ ID NO:3:

(i) SEQUENCE CHARACTERISTICS:
        (A) LENGTH: 8136 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

| | |
|---|---|
| GCGCGCGTTG ACATTGATTA TTGACTAGTT ATTAATAGTA ATCAATTACG GGGTCATTAG | 60 |
| TTCATAGCCC ATATATGGAG TTCCGCGTTA CATAACTTAC GGTAAATGGC CCGCCTGGCT | 120 |
| GACCGCCCAA CGACCCCCGC CCATTGACGT CAATAATGAC GTATGTTCCC ATAGTAACGC | 180 |
| CAATAGGGAC TTTCCATTGA CGTCAATGGG TGGACTATTT ACGGTAAACT GCCCACTTGG | 240 |
| CAGTACATCA AGTGTATCAT ATGCCAAGTA CGCCCCCTAT TGACGTCAAT GACGGTAAAT | 300 |
| GGCCCGCCTG GCATTATGCC CAGTACATGA CCTTATGGGA CTTTCCTACT TGGCAGTACA | 360 |
| TCTACGTATT AGTCATCGCT ATTACCATGG TGATGCGGTT TTGGCAGTAC ATCAATGGGC | 420 |
| GTGGATAGCG GTTTGACTCA CGGGGATTTC CAAGTCTCCA CCCCATTGAC GTCAATGGGA | 480 |
| GTTTGTTTTG GCACCAAAAT CAACGGGACT TTCCAAAATG TCGTAACAAC TCCGCCCCAT | 540 |
| TGACGCAAAT GGGCGGTAGG CGTGTACGGT GGGAGGTCTA TATAAGCAGA GCTCTCTGGC | 600 |
| TAACTAGAGA ACCCACTGCT TACTGGCTTA TCGAAATTAA TACGACTCAC TATAGGGAGA | 660 |
| CCCAAGCTTG GTACCGAGCT CGGATCCACT AGTAACGGCC GCCAGTGTGC TGGAATTCGG | 720 |
| CTTATTCATG ATAGATCCCG TCGTTTTACA ACGTCGTGAC TGGGAAAACC CTGGCGTTAC | 780 |
| CCAACTTAAT CGCCTTGCAG CACATCCCCC TTTCGCCAGC TGGCGTAATA GCGAAGAGGC | 840 |
| CCGCACCGAT CGCCCTTCCC AACAGTTGCG CAGCCTGAAT GGCGAATGGC GCTTTGCCTG | 900 |
| GTTTCCGGTA CCAGAAGCGG TGCCGGAAAG CTGGCTGGAG TGCGATCTTC CTGAGGCCGA | 960 |
| TACTGTCGTC GTCCCCTCAA ACTGGCAGAT GCACGGTTAC GATGCGCCCA TCTACACCAA | 1020 |
| CGTAACCTAT CCCATTACGG TCAATCCGCC GTTTGTTCCC ACGGAGAATC CGACGGGTTG | 1080 |
| TTACTCGCTC ACATTTAATG TTGATGAAAG CTGGCTACAG GAAGGCCAGA CGCGAATTAT | 1140 |

```
TTTTGATGGC GTTAACTCGG CGTTTCATCT GTGGTGCAAC GGGCGCTGGG TCGGTTACGG    1200

CCAGGACAGT CGTTTGCCGT CTGAATTTGA CCTGAGCGCA TTTTTACGCG CCGGAGAAAA    1260

CCGCCTCGCG GTGATGGTGC TGCGTTGGAG TGACGGCAGT TATCTGGAAG ATCAGGATAT    1320

GTGGCGGATG AGCGGCATTT TCCGTGACGT CTCGTTGCTG CATAAACCGA CTACACAAAT    1380

CAGCGATTTC CATGTTGCCA CTCGCTTTAA TGATGATTTC AGCCGCGCTG TACTGGAGGC    1440

TGAAGTTCAG ATGTGCGGCG AGTTGCGTGA CTACCTACGG GTAACAGTTT CTTTATGGCA    1500

GGGTGAAACG CAGGTCGCCA GCGGCACCGC GCCTTTCGGC GGTGAAATTA TCGATGAGCG    1560

TGGTGGTTAT GCCGATCGCG TCACACTACG TCTGAACGTC GAAAACCCGA AACTGTGGAG    1620

CGCCGAAAATC CCGAATCTCT ATCGTGCGGT GGTTGAACTG CACACCGCCG ACGGCACGCT    1680

GATTGAAGCA GAAGCCTGCG ATGTCGGTTT CCGCGAGGTG CGGATTGAAA ATGGTCTGCT    1740

GCTGCTGAAC GGCAAGCCGT TGCTGATTCG AGGCGTTAAC CGTCACGAGC ATCATCCTCT    1800

GCATGGTCAG GTCATGGATG AGCAGACGAT GGTGCAGGAT ATCCTGCTGA TGAAGCAGAA    1860

CAACTTTAAC GCCGTGCGCT GTTCGCATTA TCCGAACCAT CCGCTGTGGT ACACGCTGTG    1920

CGACCGCTAC GGCCTGTATG TGGTGGATGA AGCCAATATT GAAACCCACG GCATGGTGCC    1980

AATGAATCGT CTGACCGATG ATCCGCGCTG GCTACCGGCG ATGAGCGAAC GCGTAACGCG    2040

AATGGTGCAG CGCGATCGTA ATCACCCGAG TGTGATCATC TGGTCGCTGG GGAATGAATC    2100

AGGCCACGGC GCTAATACG ACGCGCTGTA TCGCTGGATC AAATCTGTCG ATCCTTCCCG    2160

CCCGGTGCAG TATGAAGGCG GCGGAGCCGA CACCACGGCC ACCGATATTA TTTGCCCGAT    2220

GTACGCGCGC GTGGATGAAG ACCAGCCCTT CCCGGCTGTG CCGAAATGGT CCATCAAAAA    2280

ATGGCTTTCG CTACCTGGAG AGACGCGCCC GCTGATCCTT TGCGAATACG CCCACGCGAT    2340

GGGTAACAGT CTTGGCGGTT TCGCTAAATA CTGGCAGGCG TTTCGTCAGT ATCCCCGTTT    2400

ACAGGGCGGC TTCGTCTGGG ACTGGGTGGA TCAGTCGCTG ATTAAATATG ATGAAAACGG    2460

CAACCCGTGG TCGGCTTACG GCGGTGATTT TGGCGATACG CCGAACGATC GCCAGTTCTG    2520

TATGAACGGT CTGGTCTTTG CCGACCGCAC GCCGCATCCA GCGCTGACGG AAGCAAAACA    2580

CCAGCAGCAG TTTTTCCAGT TCCGTTTATC CGGGCAAACC ATCGAAGTGA CCAGCGAATA    2640

CCTGTTCCGT CATAGCGATA ACGAGCTCCT GCACTGGATG GTGGCGCTGG ATGGTAAGCC    2700

GCTGGCAAGC GGTGAAGTGC CTCTGGATGT CGCTCCACAA GGTAAACAGT TGATTGAACT    2760

GCCTGAACTA CCGCAGCCGG AGAGCGCCGG GCAACTCTGG CTCACAGTAC GCGTAGTGCA    2820

ACCGAACGCG ACCGCATGGT CAGAAGCCGG GCACATCAGC GCCTGGCAGC AGTGGCGTCT    2880

GGCGGAAAAC CTCAGTGTGA CGCTCCCCGC CGCGTCCCAC GCCATCCCGC ATCTGACCAC    2940

CAGCGAAATG GATTTTTGCA TCGAGCTGGG TAATAAGCGT TGGCAATTTA ACCGCCAGTC    3000

AGGCTTTCTT TCACAGATGT GGATTGGCGA TAAAAAACAA CTGCTGACGC CGCTGCGCGA    3060

TCAGTTCACC CGTGCACCGC TGGATAACGA CATTGGCGTA AGTGAAGCGA CCCGCATTGA    3120

CCCTAACGCC TGGGTCGAAC GCTGGAAGGC GGCGGGCCAT TACCAGGCCG AAGCAGCGTT    3180

GTTGCAGTGC ACGGCAGATA CACTTGCTGA TGCGGTGCTG ATTACGACCG CTCACGCGTG    3240

GCAGCATCAG GGGAAAACCT TATTTATCAG CCGGAAAACC TACCGGATTG ATGGTAGTGG    3300

TCAAATGGCG ATTACCGTTG ATGTTGAAGT GGCGAGCGAT ACACCGCATC CGGCGCGGAT    3360

TGGCCTGAAC TGCCAGCTGG CGCAGGTAGC AGAGCGGGTA AACTGGCTCG GATTAGGGCC    3420

GCAAGAAAAC TATCCCGACC GCCTTACTGC CGCCTGTTTT GACCGCTGGG ATCTGCCATT    3480

GTCAGACATG TATACCCCGT ACGTCTTCCC GAGCGAAAAC GGTCTGCGCT GCGGGACGCG    3540
```

```
CGAATTGAAT TATGGCCCAC ACCAGTGGCG CGGCGACTTC CAGTTCAACA TCAGCCGCTA     3600

CAGTCAACAG CAACTGATGG AAACCAGCCA TCGCCATCTG CTGCACGCGG AAGAAGGCAC     3660

ATGGCTGAAT ATCGACGGTT TCCATATGGG GATTGGTGGC GACGACTCCT GGAGCCCGTC     3720

AGTATCGGCG GAATTCCAGC TGAGCGCCGG TCGCTACCAT TACCAGTTGG TCTGGTGTCA     3780

AAAATAAGCC GAATTCTGCA GATATCCATC ACACTGGCGG CCGCTCGAGC ATGCATCTAG     3840

AGGGCCCTAT TCTATAGTGT CACCTAAATG CTAGAGCTCG CTGATCAGCC TCGACTGTGC     3900

CTTCTAGTTG CCAGCCATCT GTTGTTTGCC CCTCCCCCGT GCCTTCCTTG ACCCTGGAAG     3960

GTGCCACTCC CACTGTCCTT TCCTAATAAA ATGAGGAAAT TGCATCGCAT TGTCTGAGTA     4020

GGTGTCATTC TATTCTGGGG GGTGGGGTGG GGCAGGACAG CAAGGGGGAG GATTGGGAAG     4080

ACAATAGCAG GCATGCTGGG GATGCGGTGG GCTCTATGGC TTCTGAGGCG GAAAGAACCA     4140

GTGGCGGTAA TACGGTTATC CACAGAATCA GGGGATAACG CAGGAAAGAA CATGTGAGCA     4200

AAAGGCCAGC AAAAGGCCAG GAACCGTAAA AAGGCCGCGT TGCTGGCGTT TTTCCATAGG     4260

CTCCGCCCCC CTGACGAGCA TCACAAAAAT CGACGCTCAA GTCAGAGGTG GCGAAACCCG     4320

ACAGGACTAT AAAGATACCA GGCGTTTCCC CCTGGAAGCT CCCTCGTGCG CTCTCCTGTT     4380

CCGACCCTGC CGCTTACCGG ATACCTGTCC GCCTTTCTCC CTTCGGGAAG CGTGGCGCCT     4440

TCTCATAGCT CACGCTGTAG GTATCTCAGT TCGGTGTAGG TCGTTCGCTC CAAGCTGGGC     4500

TGTGTGCACG AACCCCCCGT TCAGCCCGAC CGCTGCGCCT TATCCGGTAA CTATCGTCTT     4560

GAGTCCAACC CGGTAAGACA CGACTTATCG CCACTGGCAG CAGCCACTGG TAACAGGATT     4620

AGCAGAGCGA GGTATGTAGG CGGTGCTACA GAGTTCTTGA AGTGGTGGCC TAACTACGGC     4680

TACACTAGAA GGACAGTATT TGGTATCTGC GCTCTGCTGA AGCCAGTTAC CTTCGGAAAA     4740

AGAGTTGGTA GCTCTTGATC CGGCAAACAA ACCACCGCTG GTAGCGGTGG TTTTTTTGTT     4800

TGCAAGCAGC AGATTACGCG CAGAAAAAAA GGATCTCAAG AAGATCCTTT GATCTTTTCT     4860

ACGGGGTCTG ACGCTCAGTG GAACGAAAAC TCACGTTAAG GGATTTTGGT CATGAGATTA     4920

TCAAAAGGA TCTTCACCTA GATCCTTTTA AATTAAAAAT GAAGTTTTAA ATCAATCTAA     4980

AGTATATATG AGTAACCTGA GGCTATGGCA GGGCCTGCCG CCCCGACGTT GGCTGCGAGC     5040

CCTGGGCCTT CACCCGAACT TGGGGGGTGG GGTGGGGAAA AGGAAGAAAC GCGGGCGTAT     5100

TGGCCCCAAT GGGGTCTCGG TGGGGTATCG ACAGAGTGCC AGCCCTGGGA CCGAACCCCG     5160

CGTTTATGAA CAAACGACCC AACACCGTGC GTTTTATTCT GTCTTTTTAT TGCCGTCATA     5220

GCGCGGGTTC CTTCCGGTAT TGTCTCCTTC CGTGTTTCAG TTAGCCTCCC CCTAGGGTGG     5280

GCGAAGAACT CCAGCATGAG ATCCCCGCGC TGGAGGATCA TCCAGCCGGC GTCCGGAAA     5340

ACGATTCCGA AGCCCAACCT TTCATAGAAG GCGGCGGTGG AATCGAAATC TCGTGATGGC     5400

AGGTTGGGCG TCGCTTGGTC GGTCATTTCG AACCCCAGAG TCCCGCTCAG AAGAACTCGT     5460

CAAGAAGGCG ATAGAAGGCG ATGCGCTGCG AATCGGGAGC GGCGATACCG TAAAGCACGA     5520

GGAAGCGGTC AGCCCATTCG CCGCCAAGCT CTTCAGCAAT ATCACGGGTA GCCAACGCTA     5580

TGTCCTGATA GCGGTCCGCC ACACCCAGCC GGCCACAGTC GATGAATCCA GAAAAGCGGC     5640

CATTTTCCAC CATGATATTC GGCAAGCAGG CATCGCCATG GGTCACGACG AGATCCTCGC     5700

CGTCGGGCAT GCTCGCCTTG AGCCTGGCGA ACAGTTCGGC TGGCGCGAGC CCCTGATGCT     5760

CTTGATCATC CTGATCGACA AGACCGGCTT CCATCCGAGT ACGTGCTCGC TCGATGCGAT     5820

GTTTCGCTTG GTGGTCGAAT GGGCAGGTAG CCGGATCAAG CGTATGCAGC CGCCGCATTG     5880

CATCAGCCAT GATGGATACT TTCTCGGCAG GAGCAAGGTG AGATGACAGG AGATCCTGCC     5940
```

```
CCGGCACTTC GCCCAATAGC AGCCAGTCCC TTCCCGCTTC AGTGACAACG TCGAGCACAG    6000

CTGCGCAAGG AACGCCCGTC GTGGCCAGCC ACGATAGCCG CGCTGCCTCG TCTTGCAGTT    6060

CATTCAGGGC ACCGGACAGG TCGGTCTTGA CAAAAAGAAC CGGGCGCCCC TGCGCTGACA    6120

GCCGGAACAC GGCGGCATCA GAGCAGCCGA TTGTCTGTTG TGCCCAGTCA TAGCCGAATA    6180

GCCTCTCCAC CCAAGCGGCC GGAGAACCTG CGTGCAATCC ATCTTGTTCA ATCATGCGAA    6240

ACGATCCTCA TCCTGTCTCT TGATCGATCT TTGCAAAAGC CTAGGCCTCC AAAAAAGCCT    6300

CCTCACTACT TCTGGAATAG CTCAGAGGCC GAGGCGGCCT CGGCCTCTGC ATAAATAAAA    6360

AAAATTAGTC AGCCATGGGG CGGAGAATGG GCGGAACTGG GCGGAGTTAG GGGCGGGATG    6420

GGCGGAGTTA GGGGCGGGAC TATGGTTGCT GACTAATTGA GATGCATGCT TTGCATACTT    6480

CTGCCTGCTG GGGAGCCTGG GGACTTTCCA CACCTGGTTG CTGACTAATT GAGATGCATG    6540

CTTTGCATAC TTCTGCCTGC TGGGGAGCCT GGGGACTTTC CACACCCTAA CTGACACACA    6600

TTCCACAGCT GGTTCTTTCC GCCTCAGGAC TCTTCCTTTT TCAATAAATC AATCTAAAGT    6660

ATATATGAGT AAACTTGGTC TGACAGTTAC CAATGCTTAA TCAGTGAGGC ACCTATCTCA    6720

GCGATCTGTC TATTTCGTTC ATCCATAGTT GCCTGACTCC CCGTCGTGTA GATAACTACG    6780

ATACGGGAGG GCTTACCATC TGGCCCCAGT GCTGCAATGA TACCGCGAGA CCCACGCTCA    6840

CCGGCTCCAG ATTTATCAGC AATAAACCAG CCAGCCGGAA GGGCCGAGCG CAGAAGTGGT    6900

CCTGCAACTT TATCCGCCTC CATCCAGTCT ATTAATTGTT GCCGGGAAGC TAGAGTAAGT    6960

AGTTCGCCAG TTAATAGTTT GCGCAACGTT GTTGCCATTG CTACAGGCAT CGTGGTGTCA    7020

CGCTCGTCGT TTGGTATGGC TTCATTCAGC TCCGGTTCCC AACGATCAAG GCGAGTTACA    7080

TGATCCCCCA TGTTGTGCAA AAAAGCGGTT AGCTCCTTCG GTCCTCCGAT CGTTGTCAGA    7140

AGTAAGTTGG CCGCAGTGTT ATCACTCATG GTTATGGCAG CACTGCATAA TTCTCTTACT    7200

GTCATGCCAT CCGTAAGATG CTTTTCTGTG ACTGGTGAGT ACTCAACCAA GTCATTCTGA    7260

GAATAGTGTA TGCGGCGACC GAGTTGCTCT TGCCCGGCGT CAATACGGGA TAATACCCGC    7320

CCACATAGCA GAACTTTAAA AGTGCTCATC ATTGGAAAAC GTTCTTCGGG GCGAAAACTC    7380

TCAAGGATCT TACCGCTGTT GAGATCCAGT TCGATGTAAC CCACTCGTGC ACCCAACTGA    7440

TCTTCAGCAT CTTTTACTTT CACCAGCGTT TCTGGGTGAG CAAAAACAGG AAGGCAAAAT    7500

GCCGCAAAAA AGGGAATAAG GGCGACACGG AAATGTTGAA TACTCATACT CTTCCTTTTT    7560

CAATATTATT GAAGCATTTA TCAGGGTTAT TGTCTCATGA GCGGATACAT ATTTGAATGT    7620

ATTTAGAAAA ATAAACAAAT AGGGGTTCCG CGCACATTTC CCCGAAAAGT GCCACCTGAC    7680

GCGCCCTGTA GCGGCGCATT AAGCGCGGCG GGTGTGGTGG TTACGCGCAG CGTGACCGCT    7740

ACACTTGCCA GCGCCCTAGC GCCCGCTCCT TTCGCTTTCT TCCCTTCCTT TCTCGCCACG    7800

TTCGCCGGCT TTCCCCGTCA AGCTCTAAAT CGGGGGCTCC CTTTAGGGTT CCGATTTAGT    7860

GCTTTACGGC ACCTCGACCC CAAAAAACTT GATTAGGGTG ATGGTTCACG TAGTGGGCCA    7920

TCGCCCTGAT AGACGGTTTT TCGCCCTTTG ACGTTGGAGT CCACGTTCTT TAATAGTGGA    7980

CTCTTGTTCC AAACTGGAAC AACACTCAAC CCTATCTCGG TCTATTCTTT TGATTTATAA    8040

GGGATTTTGC CGATTTCGGC CTATTGGTTA AAAAATGAGC TGATTTAACA AAAATTTAAC    8100

GCGAATTTTA ACAAAATATT AACGCTTACA ATTTAC                               8136
```

(2) INFORMATION FOR SEQ ID NO:4:

(i) SEQUENCE CHARACTERISTICS:
        (A) LENGTH: 11 amino acids

```
        (B) TYPE: amino acid
        (C) STRANDEDNESS: single
        (D) TOPOLOGY: linear (xi) SEQUENCE DESCRIPTION: SEQ ID NO:4:

Glu Gln Lys Leu Ile Ser Glu Glu Asp Leu Asn
1               5                   10

(2) INFORMATION FOR SEQ ID NO:5:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:5:

Met Glu Thr Asp Thr Leu Leu Leu Trp Val Leu Leu Leu Trp Val Pro Gly
1               5                   10                  15

Ser Thr Gly Asp
        20

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:6:

Tyr Pro Tyr Asp Val Pro Asp Tyr Ala
1               5
```